US012640241B2

(12) United States Patent
Long et al.

(10) Patent No.: US 12,640,241 B2
(45) Date of Patent: May 26, 2026

(54) SYSTEMS AND METHODS FOR DETERMINING PATIENT HOSPITALIZATION RISK AND TREATING PATIENTS

(71) Applicant: Fresenius Medical Care Holdings, Inc., Waltham, MA (US)

(72) Inventors: Andrew W. Long, Brookline, MA (US); Thomas C. Blanchard, Somerville, MA (US); Len Usvyat, Boston, MA (US); Hernando G. Garza, Concord, CA (US); Jodi Conti, Lakeway, TX (US); Cara S. Gallagher, Leander, TX (US); Joanna L. Willetts, Framingham, MA (US); Hao Han, Lexington, MA (US); Sheetal Chaudhuri, Arlington, MA (US); Franklin W. Maddux, Lincoln, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/289,450

(22) Filed: Feb. 28, 2019

(65) Prior Publication Data

US 2020/0051674 A1      Feb. 13, 2020

Related U.S. Application Data

(60) Provisional application No. 62/637,332, filed on Mar. 1, 2018, provisional application No. 62/716,034, filed on Aug. 8, 2018.

(51) Int. Cl.
| | |
|---|---|
| *G16H 10/60* | (2018.01) |
| *G16H 20/40* | (2018.01) |
| *G16H 50/30* | (2018.01) |

(52) U.S. Cl.
CPC ............. *G16H 10/60* (2018.01); *G16H 20/40* (2018.01); *G16H 50/30* (2018.01)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS

| | | | |
|---|---|---|---|
| 2006/0167654 A1 | 7/2006 | Keinan et al. | |
| 2006/0167784 A1* | 7/2006 | Hoffberg .............. | G06Q 20/401 |
| | | | 705/37 |

(Continued)

FOREIGN PATENT DOCUMENTS

| | | |
|---|---|---|
| CA | 3008904 A1 | 6/2017 |
| WO | 2017106558 A1 | 6/2017 |

OTHER PUBLICATIONS

Titapiccolo et al., "Mining Medical Data to Develop Clinical Decision Making Tools in Hemodialysis," 2012 IEEE 12th International Conference on Data Mining Workshops, Brussels, Belgium, 2012, pp. 99-106, doi: 10.1109/ICDMW.2012.55.*
(Continued)

*Primary Examiner* — Robert W Morgan
*Assistant Examiner* — Charles P Coleman
(74) *Attorney, Agent, or Firm* — Leydig, Voit & Mayer, Ltd.

(57) ABSTRACT

A system and method for determining patient hospitalization risk and treating patients is disclosed. The system and method may include extracting patient data from one or more databases corresponding to a pool of patients having end stage renal disease; using a predictive model with the extracted patient data to generate, for each of the patients, a respective expected probability for hospitalization within a predetermined time period; identifying a subset of patients
(Continued)

having respective expected probabilities that are higher than other patients in the pool of patients; identifying, for each patient, at least one factor from the patient data that increased the expected probability of hospitalization; and based on the identified factors, determining and executing clinical interventions to lower the probability of hospitalization within the subset of the pool of patients.

20 Claims, 21 Drawing Sheets

(58) Field of Classification Search
CPC ........ G16H 20/17; G16H 30/00; G16H 40/00; G16H 50/00; G16H 70/00; G16H 80/00; G16H 10/60; G16H 20/40; G16H 50/30; G06Q 50/22; G06Q 50/23; G06Q 50/24
USPC .................................................. 705/3, 2, 20
See application file for complete search history.

(56) References Cited

U.S. PATENT DOCUMENTS

| | | | |
|---|---|---|---|
| 2010/0023307 A1* | 1/2010 | Lee ..................... | G06F 18/2321 703/7 |
| 2013/0144642 A1* | 6/2013 | Bessette ................ | G06F 19/328 705/2 |
| 2013/0262357 A1* | 10/2013 | Amarasingham ...... | G16H 50/70 706/21 |
| 2014/0278546 A1 | 9/2014 | Op Den Buijs et al. | |
| 2015/0213217 A1* | 7/2015 | Amarasingham ...... | G16H 50/30 705/2 |
| 2015/0213224 A1* | 7/2015 | Amarasingham ....... | G06F 19/00 705/2 |
| 2015/0213225 A1* | 7/2015 | Amarasingham ....... | G06F 19/00 705/2 |
| 2016/0357923 A1* | 12/2016 | Dong ..................... | G16H 50/20 |
| 2017/0083682 A1* | 3/2017 | McNutt ................ | A61N 5/1038 |
| 2018/0158552 A1* | 6/2018 | Liu .......................... | G06N 3/045 |
| 2018/0166174 A1* | 6/2018 | Lewis .................... | G16H 50/70 |
| 2018/0374581 A1* | 12/2018 | Berringer ................ | G06F 19/00 |
| 2019/0034590 A1* | 1/2019 | Oren ...................... | G16H 15/00 |
| 2019/0192052 A1* | 6/2019 | Weffers-Albu ........ | A61B 5/165 |
| 2019/0213685 A1* | 7/2019 | Ironside ................. | G06N 20/00 |
| 2019/0378210 A1* | 12/2019 | Merrill ................... | G06N 3/084 |
| 2022/0005041 A1* | 1/2022 | Chang .................... | G06F 18/24 |
| 2022/0181027 A1* | 6/2022 | Ackerman ............. | G16H 50/20 |

OTHER PUBLICATIONS

Cornalba et al., "Building a Normative Decision Support System for Clinical and Operational Risk Management in Hemodialysis," in IEEE Transactions on Information Technology in Biomedicine, vol.

12, No. 5, pp. 678-686, Sep. 2008, doi: 10.1109/TITB.2008. 920781.*

Sun et al. 2006, "Boosting Kernel Models for Regression," Sixth International Conference on Data Mining (ICDM'06), Hong Kong, China, 2006, pp. 583-591, doi: 10.1109/ICDM.2006.30.*

Natekin et al. 2013, "Gradient boosting machines, a tutorial." Frontiers in neurorobotics vol. 7 21. Dec. 4, 2013, doi: 10.3389/fnbot.2013.00021.*

Diego et al. 2016, "Structured Regression Gradient Boosting," 2016 IEEE Conference on Computer Vision and Pattern Recognition (CVPR), Las Vegas, NV, USA, 2016, pp. 1459-1467, doi: 10.1109/CVPR.2016.162.*

International Search Report and Written Opinion for International application No. PCT/US2019/020129, mailed on May 9, 2019, 17 pages.

Wick, J.P. et al, "A Clinical Risk Prediction Tool for 6-Month Mortality After Dialysis Initiation Among Older Adults", American Journal of Kidney Diseases , 69(5):568-575 (2016).

Couchoud, C., et al, "A clinical score to predict 6-month prognosis in elderly patients starting dialysis for end-stage renal disease", Nephrology Dialysis Transplant 24(5):1553-1561 (2008).

Thamer, M., et al., "Predicting Early Death Among Elderly Dialysis Patients: Development and Validation of a Risk Score to Assist Shared Decision making for Dialysis Initiation", American Journal of Kidney Diseases 66(6): 1024-1032 (2015).

Mingle, D., "Predicting Diabetic Readmission Rates: Moving Beyond Hba1c", Current Trends in Biomedical Engineering & Biosciences, 7(3):1-11 (2017).

Lundberg, S., and Lee, S-I, "A Unified Approach to Interpreting Model Predictions". Paper presented at the 31st Conference on Neural Information Processing Systems (NIPS 2017), Long Beach, CA (Nov. 2017), 10 pages.

Lundberg, S., et al., "Consistent Individualized Feature Attribution for Tree Ensembles", ACM Conference [online] London UK (Jul. 2018) [retrieved on May 14, 2019]. Retrieved from Internet URL: https://groundai.com/project/consistent-individualized-feature-attribution-for-tree-ensembles/1, 22 pages.

Couchoud, et al., Development of a risk stratification algorithm to imporve patient-centered care and decision making for incident elderly patients with end-stage renal disease, Kidney International 88(5): 1178-1186 (2015).

Mingle, D., "Predicting Diabetic Readmission Rates: Moving Beyond Hba1c", Current Trends in Biomedical Engineering & Biosciences, vol. 7, No. 3, Aug. 2017, pp. 55-65, DOI: 10.19080/CTBEB.2017. 07.555715.

Australian Examination Report No. 2, AU Application No. 2019227922, Mar. 17, 2022 (5 pages).

Couchoud et al. "Development of a risk stratification algorithm to improve patient-centered care and decision making for incident elderly patients with end-stage renal disease"—Kidney International (2015)—Sep. 2, 2015—pp. 1178-1186.

* cited by examiner

140

| Variables | Description |
|---|---|
| Treatment data | Variables measured at a treatment (e.g. vitals, dialysis adequacy, discharge location, etc.). Historical treatment variables (e.g. maximum blood pressure in last 180 days). |
| Treatment Notes | Free text notes |
| Treatment Medications | Any medication delivered in the clinic |
| Treatment RN evaluation checkboxes | Several groupings of checkboxes |
| Labs data | Last and historical lab values (e.g. Albumin, Sodium, HGB, etc.) |
| Kinetics data | Last and historical values (e.g. blood flow rate, KECN, MVT, etc.) |
| Outcomes data | Rates and days since last hospitalization, no show, ER visit or outpatient procedure |
| Patient Info | e.g. age, vintage, gender, race, ethnicity, marital status, height |
| Assessments | Comprehensive Social Worker, Comprehensive Dietician, Dietician Progress Note |

Sensor — 1240
Sensor — 1240
Sensor — 1240
Pump — 1250
Antenna — 1245
Speaker — 1230
Microphone — 1235

1205

Processor — 1210
Controller — 1206  1206
Memory — 1220
Power Source — 1225
Display — 1202
User input interface — 1215

1500

SYSTEMS AND METHODS FOR DETERMINING PATIENT HOSPITALIZATION RISK AND TREATING PATIENTS

CROSS-REFERENCE TO RELATED APPLICATIONS

This is a non-provisional of, and claims the benefit of the filing date of, pending U.S. provisional patent application No. 62/637,332, filed Mar. 1, 2018, entitled "Systems and Methods for Determining Patient Hospitalization," and is a non-provisional of, and claims the benefit of the filing date of, pending U.S. provisional patent application No. 62/716,034, filed Aug. 8, 2018, entitled "Systems and Methods for Determining Patient Hospitalization Risk," the entirety of which applications are expressly incorporated by reference herein.

FIELD

The disclosure generally relates to healthcare related systems, devices, and methods.

BACKGROUND

Traditional health care systems are based on a fee-for-service model, whereby healthcare providers are compensated on a per-treatment or per-service basis. Under this model, a healthcare provider's compensation increases when the number of provided treatments or services increases. As such, there is no financial incentive for such providers to efficiently manage the number of provided services/procedures, nor is there any financial incentive related to the overall health outcome of the patient. Such traditional systems have led to spiraling healthcare costs and inefficiencies hindering the quality of overall care of the patient.

Moreover, many patients—especially patients with chronic illnesses—engage with a variety of different entities and health care professionals in the course of their diagnosis, treatment, and long-term care management, including hospitals, clinics, laboratories, pharmacies, physicians, clinicians, and/or other specialists. The patients' treatment information may be spread across several entities, repositories, and medical professionals, which can lead to lack of communication, or miscommunication, between the various involved entities, which can detrimentally affect the treatment and health of the patient, possibly even creating life-threatening treatment conditions. Further, this uncoordinated handling of data, and the patient's overall treatment, results in inefficiencies that can lead to increased total cost of care. In this regard, traditional fee-for-service healthcare models are far from ideal with respect to care quality and economics. The latter is evidenced by the untenable continued rise in healthcare costs in the United States under the fee-for-service model.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the present disclosure. The present disclosure may include the following various aspects and embodiments.

In accordance with one or more embodiments of the present disclosure, a method for determining patient hospitalization risk and treating patients is disclosed. In one embodiment, the method comprises: extracting patient data from one or databases corresponding to a pool of patients having end stage renal disease (ESRD); using a predictive model with the extracted patient data to generate, for each of the patients in the pool of patients, a respective expected probability for hospitalization within a predetermined time period; identifying a subset of the pool of patients having respective expected probabilities that are higher than other patients in the pool of patients; identifying, for each patient of the subset of the pool of patients, at least one factor from the patient data that increased the expected probability of hospitalization; and based on the identified factors, determining and executing clinical interventions to lower the probability of hospitalization within the subset of the pool of patients, wherein the clinical interventions include at least one of (a) administering one or more dialysis treatments in addition to a patient's existing dialysis schedule, (b) extending a patient's dialysis treatment time, (c) adjusting a patient's target weight for a dialysis treatment, (d) adjusting a dialysate sodium concentration for a patient's dialysis treatment, and (e) adjusting a patient's blood pressure medication.

In this and other embodiments, the predictive model includes a gradient-boosting framework.

In this and other embodiments, the at least one factor for each patient is identified using Shapley additive explanations.

In this and other embodiments, the predetermined time period is 7 days or less.

In this and other embodiments, the extracted patient data includes a patient's demographics, a patient's laboratory values, a patient's treatment data, or a patient's comprehensive assessment, or combinations thereof.

In this and other embodiments, the patient's demographics includes the patient's date of birth, the patient's date of first dialysis, the patient's gender, the patient's race, the patient's ethnicity, or the patient's marital status, or combinations thereof.

In this and other embodiments, the patient's laboratory values include a patient's hemoglobin levels, or a patient's albumin level, or combinations thereof.

In this and other embodiments, the patient's laboratory values are provided as an average over a specified time period, a maximum value, a minimum value, a value spike, a value dip, or trending values, or combinations thereof.

In this and other embodiments, a patient's treatment data includes a patient's vitals, and wherein the patient's vitals are provided as an average over a specified time period, a maximum value, a minimum value, a value spike, a value dip, or trending valves, or combinations thereof.

In this and other embodiments, the patient's comprehensive assessment includes a patient's recent hospitalization history, a history of a patient's missed appointments, any patient's notes or complaints, a nurse's or other medical professional assessments, or any delivered medications, or combinations thereof.

In this and other embodiments, the predictive model is built from historical data from other patients.

In this and other embodiments, the method further comprises generating a report that ranks the pool of patients according to their respective expected probabilities of hospitalization, wherein the report also provides the identified factors for each respective patient. In this and other embodiments, the method further comprises providing the generated report to one or more health care providers.

In this and other embodiments, the method further comprises transmitting an automated alert to one or more health care providers, based on the expected probabilities of hospitalization.

In this and other embodiments, the pool of patients are patients of an ESRD Seamless Care Organization (ESCO).

A system for determining a risk of hospitalization for patients having end stage renal disease (ESRD) is also disclosed. In one embodiment, the system comprises an integrated care system configured to: extract patient data from one or databases corresponding to a pool of patients having end stage renal disease (ESRD); use a predictive model with the extracted patient data to generate, for each of the patients in the pool of patients, a respective expected probability for hospitalization within a predetermined time period; identify a subset of the pool of patients having respective expected probabilities that are higher than other patients in the pool of patients; identify for each patient of the subset of the pool of patients, at least one factor from the patient data that increased the expected probability of hospitalization; and generate a report that ranks the pool of patients according to their respective expected probabilities of hospitalization, wherein the report also provides the identified factors for each respective patient.

In this and other embodiments, the predictive model includes a gradient-boosting framework.

In this and other embodiments, the integrated care system is configured to identify the at least one factor for each patient using Shapley additive explanations.

In this and other embodiments, the predetermined time period is 7 days or less.

In this and other embodiments, the extracted patient data includes a patient's demographics, a patient's laboratory values, a patient's treatment data, or a patient's comprehensive assessment, or combinations thereof.

In this and other embodiments, the patient's demographics includes the patient's date of birth, the patient's date of first dialysis, the patient's gender, the patient's race, the patient's ethnicity, or the patient's marital status, or combinations thereof.

In this and other embodiments, the patient's laboratory values include a patient's hemoglobin levels, or a patient's albumin level, or combinations thereof.

In this and other embodiments, the patient's laboratory values are provided as an average over a specified time period, a maximum value, a minimum value, a value spike, a value dip, or trending values, or combinations thereof.

In this and other embodiments, a patient's treatment data includes a patient's vitals, and wherein the patient's vitals are provided as an average over a specified time period, a maximum value, a minimum value, a value spike, a value dip, or trending valves, or combinations thereof.

In this and other embodiments, the patient's comprehensive assessment includes a patient's recent hospitalization history, a history of a patient's missed appointments, any patient's notes or complaints, a nurse's or other medical professional assessments, or any delivered medications, or combinations thereof.

In this and other embodiments, the predictive model is built from historical data from other patients.

Further features and aspects are described in additional detail below with reference to the appended Figures.

BRIEF DESCRIPTION OF THE DRAWINGS

By way of example, embodiments of the disclosed methods and devices will now be described, with reference to the accompanying drawings, in which:

FIG. 1C is a diagram illustrating an exemplary embodiment of patient variables for determining a risk of hospitalization of an end-stage renal disease (ESRD) patient in accordance with the present disclosure;

DETAILED DESCRIPTION

Figures 1A, 1B:
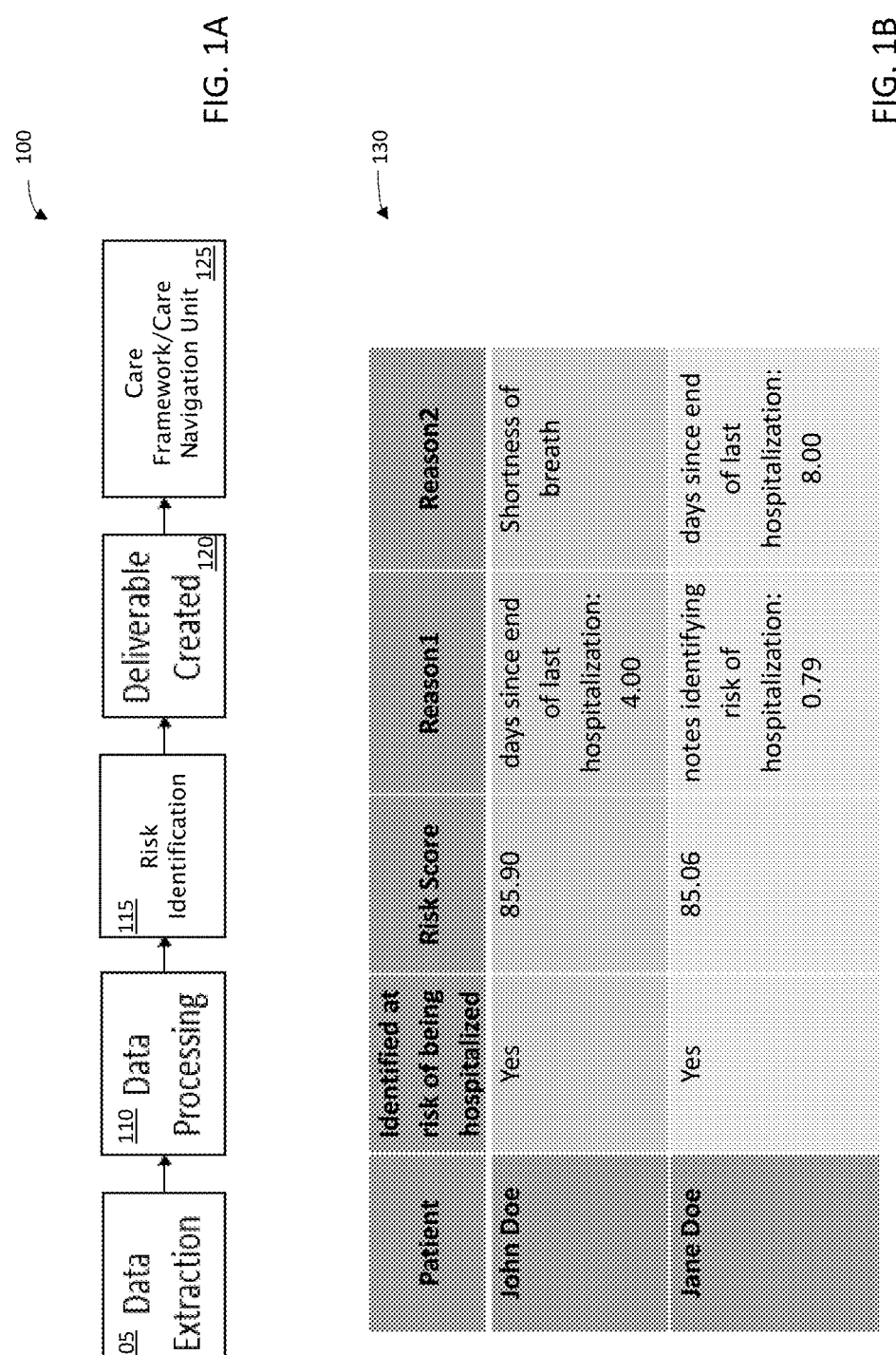
FIG. 1A is a flowchart illustrating an exemplary embodiment of a method for determining a risk of hospitalization of an end-stage renal disease (ESRD) patient in accordance with the present disclosure.
FIG. 1B is a diagram illustrating an exemplary embodiment of a report of identified patients at risk for hospitalization in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices, diagnostics, and treatments for various diseases, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Example embodiments described herein are suitable for implementing value-based care, which is an alternative to the fee-for-service healthcare model. Under a value-based healthcare system (also known as a "pay for performance" model), healthcare providers are provided with financial incentives tied to quality and efficiency of care and patient outcomes.

Some example embodiments are configured to provide coordinated care to a population of patients with a chronic disease, such as chronic kidney disease (CKD). CKD is a progressive disease marked by reduced kidney function. Once the kidney function drops below a threshold, the patient is considered to have kidney failure, or end-stage renal disease (ESRD). ESRD is the final stage of CKD and requires dialysis treatments for the remainder of the patient's life (absent a transplant).

In the United States, one model of value-based care in which example embodiments described herein may be implemented is the Comprehensive ESRD Care (CEC) Model, which is a type of accountable care organization (ACO) model developed under the authority of the U.S. Center for Medicare and Medicaid Innovation. In order to implement the CEC model, ESRD Seamless Care Organizations (ESCOs) are formed. An ESCO is an ACO that is formed by healthcare suppliers and providers voluntarily coming together. The resulting ESCO is a legal entity that provides coordinated care to ESRD beneficiaries through the CEC model.

Under the ESCO model, the ESCO shares savings and losses incurred by the U.S. Centers for Medicare and Medicaid Services (CMS) for the ESCO's beneficiaries. Savings or losses are determined by CMS based on an expenditure benchmark, which is derived from a baseline that reflects historical expenditure data for like or similar beneficiaries. The benchmark is compared to the actual Medicare Fee-For-Service (FFS) Part A and B expenditures for the aligned patient population in a performance year. The savings are also subject to an adjustment based on quality performance. Any reduction in costs directly translates to increased shared savings (profits), since the costs are measured against the predetermined benchmark. Quality of care is incentivized by the quality performance adjustment to the calculated shared savings.

The ESCO is responsible for each patient's overall care, which goes beyond dialysis treatments. For example, if a patient is admitted to the hospital for any reason (for example, infections, vascular dialysis access complications, and/or cardiac complications), the cost of the hospitalization counts against the yearly savings calculation. Since hospital admissions are especially costly, it is highly advantageous for ESCOs to keep the patients out of the hospital from a financial perspective. Example embodiments described herein implement a holistic approach to oversee and manage all aspects of the patients' well-being, which improves the quality of care while increasing efficiency of medical resources and overall cost efficiency.

Some example embodiments described herein analyze medical data of the applicable patient population in order to target high-risk patients with interventions to reduce the likelihood of hospitalization. Some examples analyze patient data to predict when a patient is likely to experience a particular health-related event or stage of disease progression and provide/adjust treatment accordingly.

In accordance with example embodiments, patient information may be sent to, managed within, and/or be accessible by, a coordinated care system, so that patients may receive high quality, efficient, coordinated health-care within a managed system that is able to intelligently manage and coordinate the patient's overall care. Incorporation of a coordinated care system may allow for better control of health care costs, e.g., by providing value-based care to patients in place of fee-for-service care. For example, as mentioned above, the population of patients diagnosed with ESRD has been increasing over time, often caused by several other diseases, including but not limited to diabetes, hypertension, and/or glomerulonephritis. Patients living with ESRD may face additional challenges due to the nature of the disease. For example, required lifestyle changes may lead to mental health deterioration. Additionally, at-home treatments may lead to increased isolation from medical professionals. As the healthcare landscape changes, opportunities to provide patients with resources for coordinating treatment may deliver additional patient health benefits beyond dialysis treatment.

Although exemplary embodiments described herein are related to renal diseases, it is understood that coordinated care systems and infrastructures described herein may be applicable to other chronic illnesses as an alternative or in addition to renal disease. Such other conditions may include, as non-limiting examples, cardiovascular related illnesses, pulmonary, gastrointestinal, neurological, urological, or gynecological conditions, diabetes, circulatory diseases, Alzheimer's or other dementias, asthma, COPD, emphysema, cancer, obesity, tobacco use, cystic fibrosis, or combinations thereof. Moreover, although some examples are described with respect to implementations in renal-related ACOs, such as ESCOs, it should be understood that the examples described herein may be analogously implemented in other ACOs with respect to other diseases or patient populations, and/or any other suitable value-based healthcare models.

An exemplary embodiment in accordance with the present disclosure may include a system for determining a risk of hospitalization of a patient suffering from kidney disease, e.g., ESRD. As described below, an integrated care system may be configured so that data (e.g., lab test results) and recorded information (e.g., treatment notes) for ESRD patients receiving dialysis treatments from clinics may be analyzed by one or more algorithms for determining a risk level of hospitalization for a patient with kidney disease, e.g., ESRD. In some embodiments, a risk of hospitalization for a patient may be imminent (e.g., within seven days). It is understood that although seven days, or one week, is used in some exemplary embodiments, imminent hospitalization of a patient may occur approximately between 1 day and 15 days, or within any predetermined amount of time, including but not limited to one month, three to six months, and the like. For example, the integrated care system may be configured to perform a method of determining a patient risk of hospitalization and generating a report by analyzing the selected patients for a risk level. FIG. 1A, for example, illustrates a flowchart of an exemplary method 100 for determining a patient risk of hospitalization. At step 105, data may be extracted. Data from the selected patients may be extracted by an integrated care system, from other clinical systems, outside systems, and/or other databases as illustrated in FIGS. 2A-11.

As described above, numerous variables may be extracted and/or assigned by the integrated care system, at step 105 of FIG. 1A, including but not limited to patient demographics, laboratory values, treatment data and/or comprehensive assessments. For example, FIG. 1C illustrates an exemplary embodiment of a chart 140 of variables which may be included for determining a patient risk of hospitalization. Patient demographics may include date of birth, date of first dialysis, gender, race, ethnicity, and marital status. Laboratory values may be data including but not limited to hemoglobin, albumin, and the like. Additionally, laboratory data may be calculated in various manners, e.g., providing an average over a specified time period, a maximum value, a minimum value, a value spike and/or dip, and trending values, for analysis by the integrated care system.

It is understood that raw data variables may be transformable through feature engineering to create additional variables and/or features, based on analysis of data patterns, and clinical experience. Treatment data may include patient vitals, e.g., blood pressure, weight, pulse, temperature, respiration rate, and like. Treatment data may also be calculatable in various manners, e.g., providing an average over a specified time period, a maximum value, a minimum value, a value spike and/or dip, and trending valves, for analysis by the integrated care system. Similar to laboratory values, raw data variables of treatment data may be transformed through feature engineering to create additional variables and/or features, based on analysis of data patterns, and clinical experience. For example, a maximum systolic blood pressure over 90 days may be calculated as a treatment data for patients.

It is understood that any number and types of patient variables may be utilized, and the variables of FIG. 1C are exemplary embodiments. In some embodiments, variables associated with patient hospitalization may include recent patient hospitalization history; engineering features related to a patient's most recent treatment; laboratory values of a patient's albumin levels, hemoglobin levels, and/or lymphocytes; a patient's vitals measured during a most recent dialysis treatment including but not limited to blood pressure, weight, and/or temperature; missed appointments (e.g., a patient was a no-show for a prescribed treatment and/or assessment) history; and/or a patient's noted and/or measured shortness of breath at a most recent dialysis treatment.

In embodiments, treatment data may further include nurse or other medical professional assessments, e.g., via checkboxes and/or text entries, delivered medications, and ancillary information, e.g., oxygen given. Comprehensive patient assessments by physicians, clinicians, and/or dieticians over selected time periods (e.g., monthly, yearly) may also be utilized. It is understood that the integrated care system may convert text entries into specified features for inclusion and analysis in the one or more algorithms.

Referring back to FIG. 1A, at step 110, extracted patient data as described with respect to FIG. 1C at step 105, may be processed by the integrated care system. The patient data for processing may be measured data, calculated data, written notes, and the like. Some of the extracted data (e.g., measured data, calculated data) is numerical, and some (e.g., clinician notes) is text and/or graphics.

In some examples, at step 110, some or all of the patient data that is in the form of numerical data may be processed to be in a more suitable form for further analysis by the integrated care system. This processing may include, for example, scaling and conversion. In some examples, this processing may include screening to ensure that the data is within a feasible range in order to filter out or identify erroneous data. In some examples, some or all of the extracted numerical data remains in its original, unmodified form through process 110.

In accordance with some embodiments, also at 110, graphical extracted data (e.g., handwritten clinician notes) is convertible to text data prior to further analysis. In some examples, this is accomplished by applying a convolutional neural network, although other suitable algorithms may be utilized in place of, or in addition to, this type of network.

The text data, including any text recognized from graphics as described above, may be processed using natural language processing techniques. These techniques may include, but are not limited to word2vec, doc2vec, continuous bag of words, or others. This processed data may then be used to train a machine learning model to identify (e.g., predict) specific outcomes, whether the outcomes are hospitalization, specific symptoms, or other medically relevant variables.

In some embodiments, as illustrated at step 115 in the example of FIG. 1C, the processed data (including any of the numeric identifiers corresponding to text data) may be sent to one or more algorithms of the integrated care system for analysis (e.g., prediction). In some examples, an algorithm may be utilized for learning from and identifying a risk (e.g., making predictions) based on the historical data (either raw or pre-processed). For example, a gradient boosting framework, and/or an extreme gradient boosting tree algorithm may be utilized. Some examples implement XGBoost. The algorithm may analyze the selected data for determining a risk score of hospitalization, e.g., identifying a risk, at step 115. As described above, patient data described in FIG. 1C may be utilized by the integrated care system to determine a risk score that each patient may be hospitalized (e.g., imminent and/or long-term hospitalization). In some examples, the algorithm (e.g., the gradient boosting framework and/or extreme gradient boosting tree algorithm) may analyze a specific patient's data in the context of the corresponding data of a pool of other patients.

In some examples, the analysis/prediction algorithm of the integrated care system may examine and analyze an entire pool of patients in order to assign for each patient a respective risk score within a predetermined time period (e.g., 7 days, weeks, months, etc.). It should be understood, however, that in some examples, the algorithm may be run for a single patient or any suitable number of selected patients from the pool.

At step 120, a document may be generatable by the care analysis and guidance system (e.g., integrated care system), by a care coordination system, and/or by a care navigation unit (see step 125 of FIG. 1A). Referring now to FIG. 1B, a report 130 may be generated by the integrated care system of the patients, e.g., ESRD patients, receiving a recent in-clinic dialysis treatment, identifying those having a risk/probability of hospitalization and/or reasons associated with the risk determination. In some embodiments, a report may indicate for the patient a risk score of hospitalization and/or the associated reasons for each patient. For example, patient John Doe may be determined by the integrated care system to be at risk for imminent hospitalization, having a calculated risk score of approximately 85.90%. Associated reasons identified by the integrated care system may include a recent hospitalization (e.g., John Doe may have been hospitalized in the last four days prior), and that the patient was determined to be experiencing a shortness of breath. It is understood that John Doe's shortness of breath may be indicated through a medical professional's notes at the dialysis treatment, and/or the integrated care system may have calculated breathing difficulties based on measured patient vitals at the dialysis treatment (e.g., blood oxygen levels, heart rate, etc.). The report 130 may further include additional patients, e.g., Jane Doe, also at risk for hospitalization. For example, Jane Doe may have a calculated risk score of 85.06% of hospitalization (e.g., imminent and/or long-term hospitalization), based on medical professional notes, and a hospitalization stay eight days prior. The report 130 may contain a list of patients associated with a physician, or clinic, or other medical professional or care provider.

In some examples, the reasons, or prominent factors, for the risk determination are determined by using Shapley additive explanations techniques, such as described in Scott M. Lundberg et al., "A Unified Approach to Interpreting Model Predictions" 2017, which is incorporated herein by reference in its entirety. This allows for determination of patient interventions that target the factors that will be most likely to impact the patient's expected likelihood of hospitalization.

In embodiments, the report 130 may be generated so that the patients are ranked according to their associated calculated risk scores. In this manner, care providers who receive the report may be alerted to patients at the highest risks. This report 130 may be provided to the care coordination system, and/or care navigation unit, at step 125 so that medical professionals may contact the identified patients and determine appropriate interventions to aid in minimizing or eliminating the hospitalization risk (see FIGS. 1D-1F). For example, if the list of reasons indicates a patient having a high temperature, the patient may have an infection. The care coordination system and/or care navigation unit may schedule an appointment for the patient with their primary care physician for testing and assessment (e.g., have cultures drawn, follow-up temperature readings, etc.).

Figure 1D:
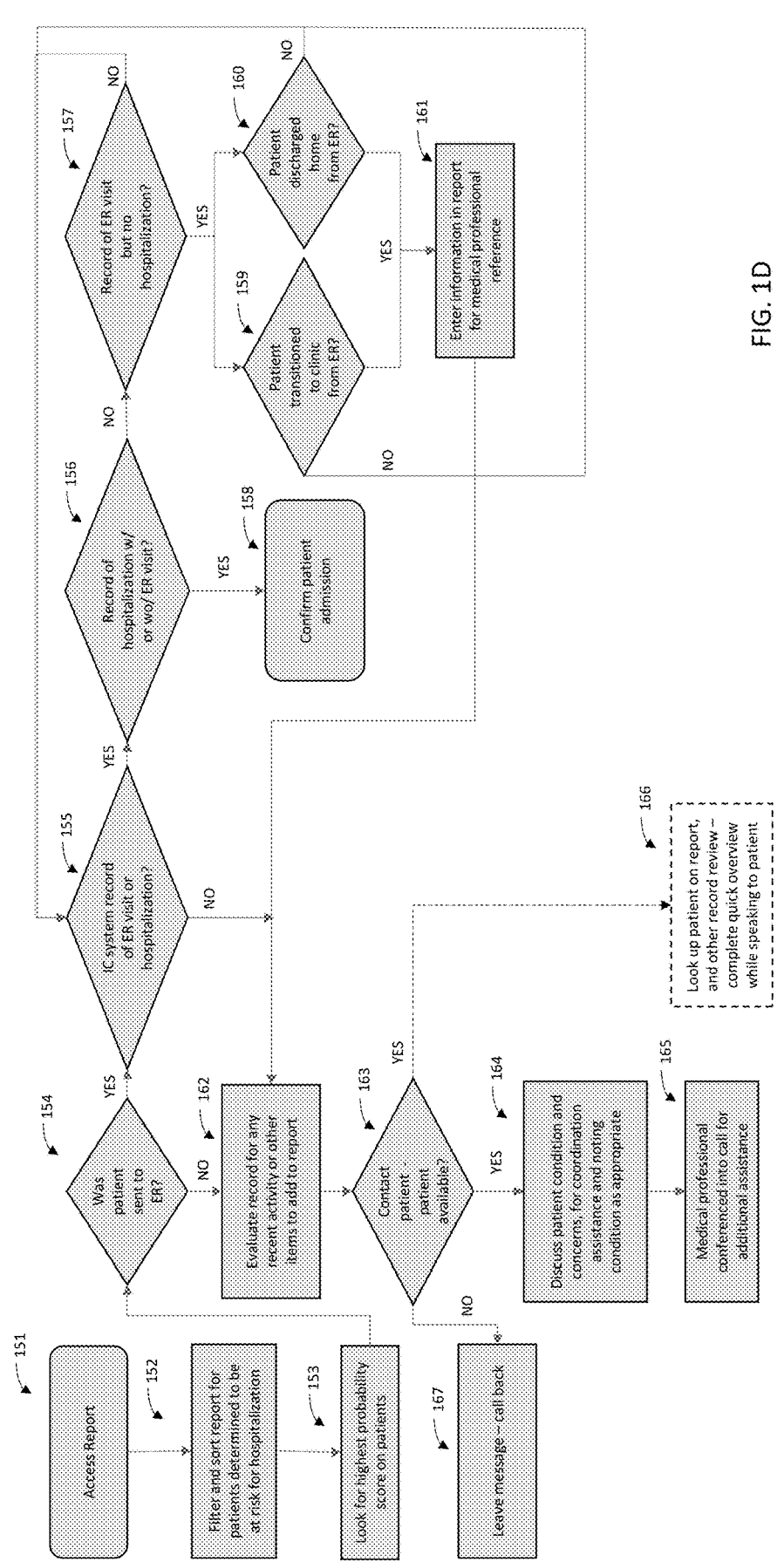
FIGS. 1D-1F are flowcharts illustrating an exemplary embodiment of a process of care coordination for a patient in accordance with the present disclosure.
Figure 1E:
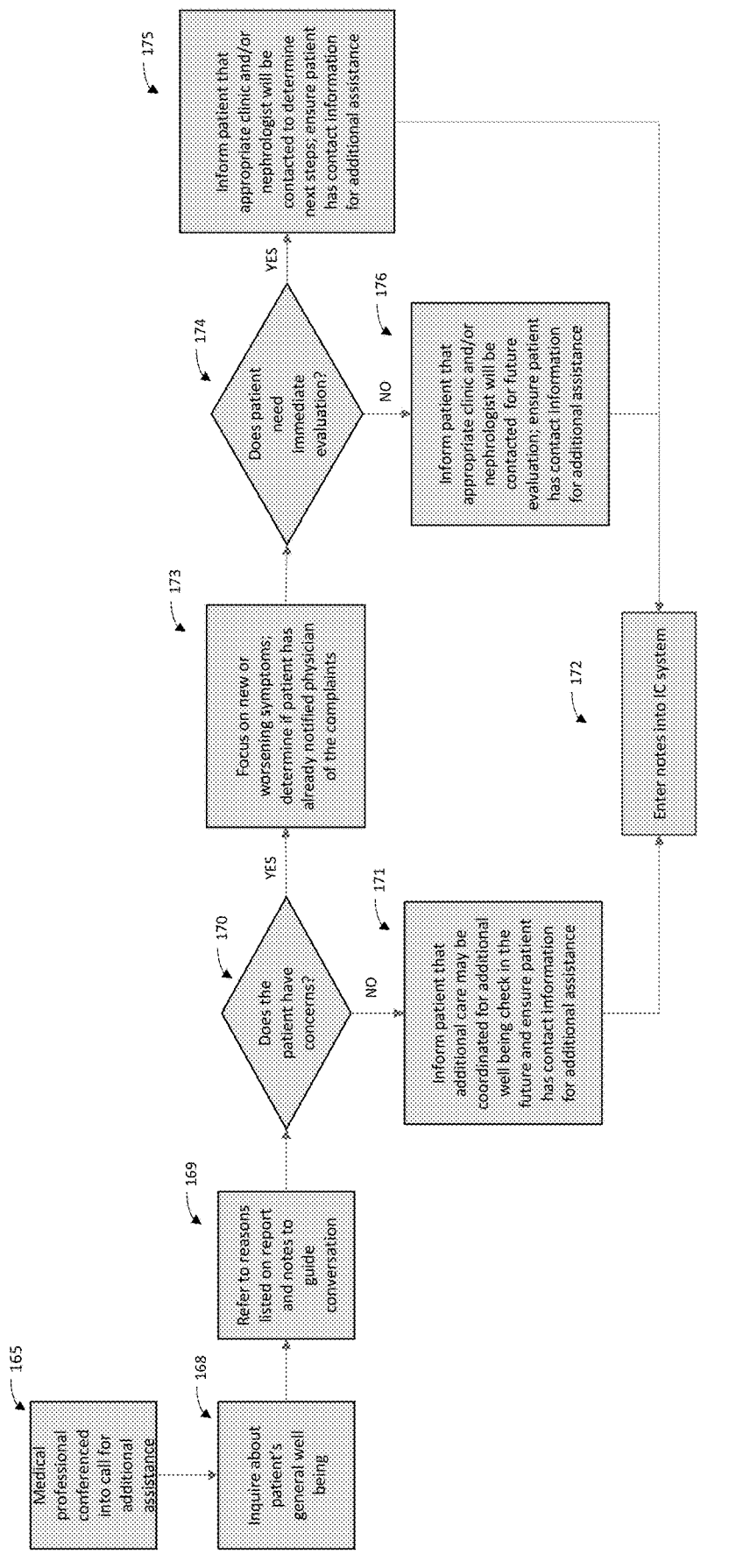
Figure 1F:
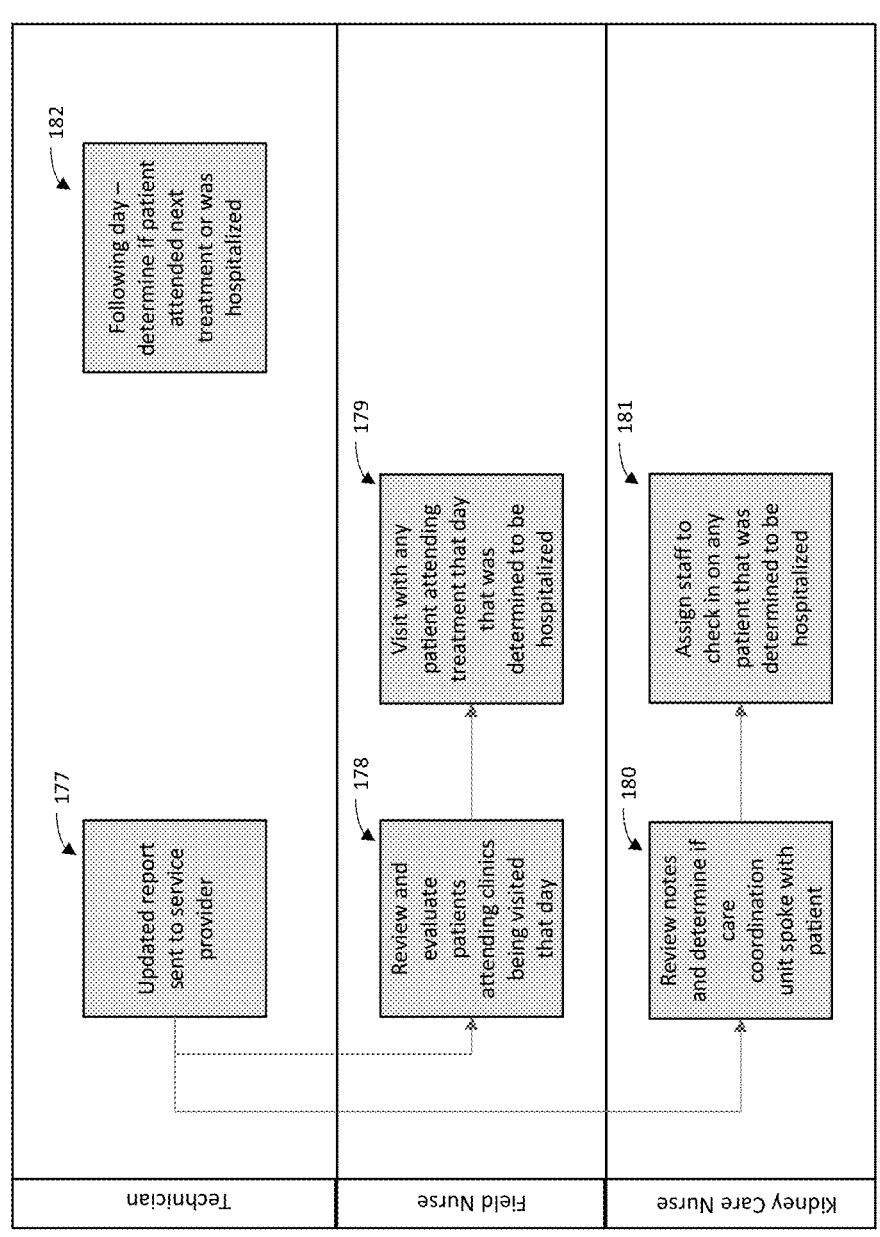

Referring now to FIGS. 1D-1F, a flowchart 150 of an exemplary embodiment of a process of the care coordination system and/or care navigation unit for handling the report and patient follow-up is shown. For example, FIG. 1D illustrates an exemplary process for coordinating patient care, for example, by technicians, care coordinators, or other service providers. Providing additional care and coordination of patient services may minimize and/or eliminate a patient's risk of hospitalization, thereby avoiding additional healthcare costs and/or improving a patient's well-being.

At step 151, the report, e.g., the report 130, may be accessed by a member of the care coordination system and/or care navigation unit. In some embodiments, the report may be accessible by a technician, a care coordinator, a service provider, and/or another health care provider. At step 152, the report 130 may be filtered and/or sorted for identifying patients determined to be at risk for hospitalization, and the risk scores of hospitalization for each patient may be evaluated at step 153.

At step 154, additional records may be evaluated for determining whether the identified patients have already been sent to an emergency room (ER), and steps 155, 156, 157 may determine whether a record of hospitalization and/or an ER visit exists in an integrated care system, and if so, if the patient visited an ER only, hospital only, or an ER visit that led to hospitalization. If, at step 156, a patient was determined to have been hospitalized, either with or without a prior visit to the ER, at step 158, the hospitalization admission may be confirmed, and the information may be entered for the patient in the integrated care system. If the patient visited an ER but was not hospitalized at step 157 the patient may have been transitioned to a clinic from the ER, or the patient may have been discharged from the ER and sent home at steps 159 and 160, respectively. In instances where the patient was transitioned to a clinic and/or discharged at steps 159 and 160, a note may be added into the report 130, for a medical professional to follow up on with the patient at step 161. In instances where the patient was not either transitioned to a clinic and/or discharged from the ER at steps 159, 160, the record in the integrated care system may be evaluated back at step 155 for determining a patient status.

If, at step 155, there is no record in the integrated care system of a hospitalization and/or an ER visit, a patient's record may be further evaluated for recent activity and/or notes or other information that should be included in the report 130 at step 162. Additionally, if at step 161 additional patient information has been included in the report 130, additional information at step 162 may be included as well.

When all the information has been added to the report 130, a member identified by the technician, care coordinator, or service provider, e.g., a nurse, clinician, physician, care coordinator, and/or other medical professional, may contact the patient at step 163, for discussion of the patient's general condition and any health concerns at step 164. If the patient is not available, a callback may be scheduled at step 167. In some embodiments, if the patient is contacted by a technician, care coordinator, or service provider, a care provider (e.g., a medical professional) may also be included in a conference call at step 165, for additional assistance. For example, the medical professional, e.g., a nurse, clinician, physician, specialist, or the like, may be able to answer any medical related questions and/or provide additional medical information to address patient concerns. The technician, care coordinator, or service provider may remain on the call to provide any additional coordination care, for example, if additional diagnostic tests need to be scheduled, or other clinicians should be involved in the patient's care as determined by the medical professional. In some embodiments, at step 166, a medical professional may be sent information, e.g., a patient's medical record number, by the care coordinator via the care coordination system of the integrated care system, for evaluation separate from the patient discussion. The medical professional may be able to assess the patient records through the integrated care system, and inform the care coordinator of any additional information to obtain from and/or provide to the patient.

FIG. 1E illustrates an exemplary process for a care provider for coordinating patient care, after step 165. For example, at step 168, an inquiry may be made into the patient's general well-being, and at step 169, the medical professional may specifically address the reasons listed on the report 130 with the patient. For example, the medical professional may assess the listed reasons and inquire directly regarding symptoms and/or other potential health concerns based on the listed reasons. The patient may also be asked if they have any health concerns that have not been addressed at step 170. If the patient does not have additional concerns, at step 171, the patient may be informed that their status may be continued to be monitored, and encouraged to contact a care coordinator if their condition changes or additional assistance is needed. It is understood that patient notes and other information from step 171 may be entered into the integrated care system at step 172.

If the patient does have additional concerns, the medical professional may be able to ascertain if the health concerns are a new condition and/or a worsening condition, and if a patient has already discussed their concerns with their primary care physician or other specialist at step 173. The medical professional may additionally determine if the patient needs immediate evaluation at step 174. For example, the medical professional may determine that the patient should be evaluated by their primary care physician, clinician, nephrologist, specialist, or other medical professional, for further evaluation and testing. If the medical professional determines that the patient needs immediate evaluation, at step 175, the patient may be informed that the appropriate parties are being informed and further steps related to scheduling and coordination may be handled by a care coordinator. If the patient does not need immediate evaluation as determined by the medical professional at step 174, at step 176 patient information may be sent to the appropriate parties (e.g., primary care physician, clinician, nephrologist, specialist, or other medical professional) for additional evaluation and potential follow-up. The patient may also be provided with contact information at steps 175, 176, and encouraged to contact a care coordinator if their condition changes or additional assistance is needed. It is understood that patient notes and other information from steps 175, 176 may be entered into the integrated care system at step 172. In some embodiments, the integrated care system may update the report 130 at step 172.

FIG. 1F illustrates an exemplary embodiment of interaction and engagement between various parties associated with the integrated care system. For example, as described with respect to FIG. 11, the care coordination system and/or the navigation unit may involve a plurality of parties for coordination of total patient treatment. As described above, a technician or service provider may include a call technician, operator, nurse, clinician, physician, care coordinator, and/or other medical professional, and each may engage with the patient individually based on the report 130, and the report 130 may be updated based on their interaction with the patient. Once the report 130 has been updated as described in flowchart 150, the report 130 may be provided to another party or service provider, e.g., a field nurse and/or a specialized nurse, including but not limited to a kidney care nurse. As shown in FIG. 1F, swim lanes for each party may define further patient engagement. For example, the updated report 130, e.g., from step 172, may be provided by a technician, care coordinator, or service provider, and sent to the responsible party at step 177. A field nurse or other medical professional may receive the updated report and determine which patients identified to be at risk for hospitalization are scheduled to attend a treatment, e.g., dialysis treatment at a clinic at step 178. At step 179, the field nurse may visit with each identified patient attending treatment, to assess in-person their condition and/or address any patient concerns. Additionally, and/or alternatively, at step 180, a specialist nurse, e.g., a kidney care nurse may review the report 130 and determine if the care navigation unit was in contact with the identified patient and, at step 181, may assign staff or other medical professional to reach out and contact the patient for a direct patient assessment. For example, in-person contact between the patient and a medical professional may allow for diagnoses and/or assessments not otherwise determinable by the report 130. This additional follow-up and care may aid in reducing and/or eliminating a hospitalization risk of the patient, which may be beneficial over the patient's long-term care. At step 182, the technician, care coordinator, or service provider may determine if any patients missed scheduled treatments, and if so, if they were hospitalized. Additional follow-up and patient contact may then be coordinated.

The report 130 may be generatable by the integrated care system for identifying and/or providing interventional treatment to patients. In some embodiments, when a report is generated, one or more patients may be identified that may benefit from predetermined treatments based on risk score levels. Care providers may assess an identified patient from the report 130 for directing additional and/or different treatments. For example, an identified patient having a high-risk score may be provided with additional services and/or treatments, which may alter their disease progression. In some patients, kidney disease progression may be slowed or even reversed by receiving timely, interventional treatment, thereby potentially minimizing or even preventing a future imminent hospitalization. The integrated care system may determine a risk of hospitalization for one or more patients, which may result in a patient receiving additional services and care in a proactive manner, potentially preempting a worsening of their kidney disease or even a hospitalization.

Figure 2A:
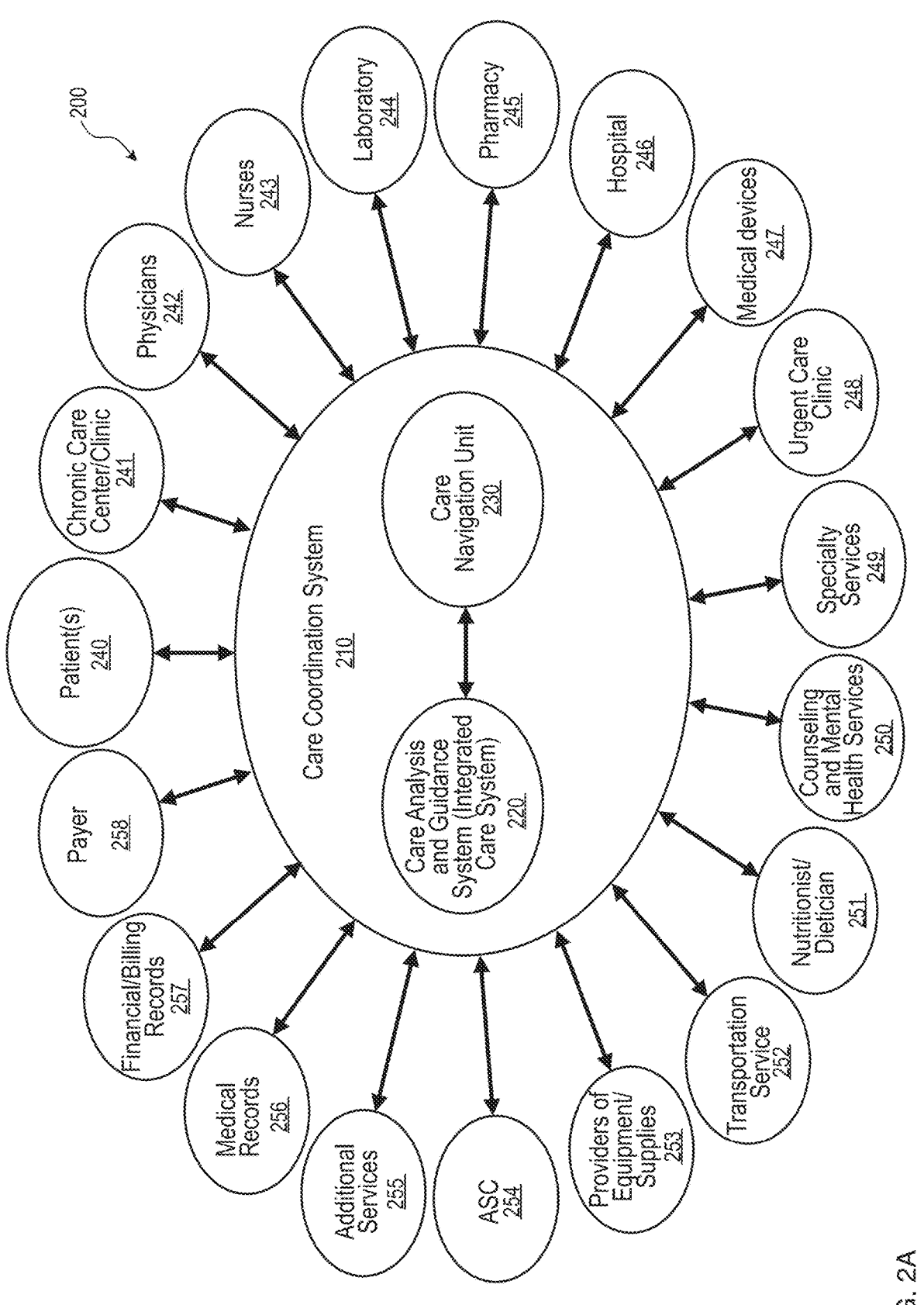
FIG. 2A is a diagram illustrating an exemplary embodiment of a system for providing coordinated healthcare in accordance with the present disclosure.

Referring to FIG. 2A, an example in accordance with the present disclosure includes a coordinated care framework 200 for treating a patient or population of patients 240. The overall care of the patient/population 240 is overseen and coordinated by a care coordination system 210. The care coordination system 210 includes a care analysis and guidance system 220 (which is referred to herein interchangeably as an "integrated care system"), which receives, analyzes, and creates data used to coordinate the care of the patient/population 240. The care coordination system 210 utilizes a care navigation unit (CNU) 230, which implements the coordinated care in accordance with data received from the care analysis and guidance system 220. To manage the overall health and well-being of the patient/population 140, the care coordination system 210 communicates with numerous relevant entities and components. In FIG. 2A, the double-arrow lines graphically represent communication and interaction flows/channels.

In the example illustrated in FIG. 2A, the care coordination system 210 coordinates care for the patients 240 among entities that include chronic care centers or clinics 241, physicians 242 (which may include nephrologists, especially for renal patients), nurses 243, laboratories 244 (e.g., blood labs or other diagnostic labs), pharmacies 245, hospitals 246, medical devices 247 (e.g., dialysis machines or other medical treatment/monitoring devices), urgent care clinics 248, specialty services 249, counseling and mental health services 250, nutritionists/dieticians 251, transportation services 252, providers of medical equipment and supplies 253, ambulatory surgical centers (ASCs) 254, additional services 255, medical records 256, financial and billing records 257, and payer(s) 258 (e.g., CMS or private insurer).

It should be understood that some example embodiments may include other entities not shown, and/or may exclude some of the entities shown. Further, it should be understood that the illustrated communication channels are not exclusive, and the various entities may also, where appropriate, communicate directly or indirectly between each other and/or the patients 240. In some examples, the communication between the care coordination system 210 and one or more of the other entities may be indirect, flowing through one or more intermediary entities. For example, coordination of nurses 243 may be conducted directly between the care coordination system 210 and the nurses 243 or via intermediary channels such as a clinic 241, 248, a hospital 246, or any other suitable channel.

In accordance with some examples, the framework 200 of FIG. 2A may be used in treating diseases such as the progression of kidney disease, e.g., End-Stage Renal Disease (ESRD) and/or Chronic Kidney Disease (CKD). Patients with ESRD are patients undergoing long-term care for kidney disease, e.g., by dialysis treatments. Patients with kidney disease, e.g., ESRD, may be hospitalized if renal treatment is not properly maintained, although some hospitalization events may be disruptive to the patient and costly, and often times may be preventable by intervention. For example, integrated care systems 220 may be used and/or configured to determine a patient hospitalization risk by identifying patients at risk and reasons for being identified at risk. Monitoring health status trends of dialysis patients may pose challenges. For example, patients may exhibit varying and irregular degrees of functional/cognitive impairment, and may be coupled with complex clinical abnormalities that are independent of a patient's length of time on dialysis. By determining a hospitalization risk of a patient, the integrated care system may identify a patient for additional and/or different treatment options. In accordance with exemplary embodiments of the present disclosure, coordinated care framework 200, including care analysis and guidance system 220, a patient may delay and/or altogether avoid a hospitalization by receiving timely interventional treatment to potentially slow and/or reverse kidney disease progression.

A care analysis and guidance system (integrated care system) 220 may include and execute various healthcare-related models and/or programs. In some examples, these models and/or programs are specifically adapted to implement or carry out particular value-based care frameworks (for example, ESCO models, other ACO models, Chronic Special Needs Plans (C-SNP's), and the like), whereas other examples may include models/programs generally applicable across multiple value-based care frameworks. It is also understood that additional types of value-based care models may be provided for other chronic illnesses, including but not limited to chronic kidney disease, or one or more of the other chronic diseases and conditions mentioned above. These healthcare models may influence improvements in providing value-based care to a patient, for example, by more efficiently managing a patient's care within a specified structure, and may replace conventional fee-for-service (FFS) models. Fee-for-service models may typically focus on volume over the quality of individualized patient care, with little incentive to improve a patient's overall health, which may be less efficient and have lower effectiveness than value-based models.

Shifting patient care away from conventional fee-for-service models to value-based healthcare models may improve care received by patients, reduce total costs, and may improve management of large patient populations diagnosed with the same chronic disease. For example, as mentioned above, value-based healthcare models may pay providers based on a quality of care (e.g., clinical outcomes, meeting specific performance criteria, etc.) received by the patients, and providers and patients may benefit from a focus on addressing and improving the overall health of patients. For example, CMS may set a budget for patient care for a diagnosed illness (e.g., ESRD), thereby incentivizing healthcare providers for innovations to lower costs in providing treatment to the illness. In some embodiments, payments may be associated, or negotiated through "shared risk" contracts, in which the cost, as well as savings, associated with an illness and the coordinated care of a patient is shared by the provider as well as the payer. This arrangement is present in the ESCO model described in greater detail above.

In some embodiments, a care coordination system may identify, test, and/or evaluate innovations through the CEC/ESCO framework for improving patient care to Medicare beneficiaries diagnosed with ESRD. The care coordination system may provide a structure for dialysis clinics, nephrologists or other specialists, and/or other providers to be connected to each other for care coordination for aligned beneficiaries. Value-based healthcare models may incentivize providers based on a quality of care of services delivered. For example, the care coordination system may incorporate incentives for improved care coordination, individualized patient care, and/or improved long-term health outcomes of a patient population. The care coordination system may also coordinate outcomes, e.g., clinical quality, financial, etc., measured by Medicare Part A (e.g., hospital insurance) and B (e.g., medical insurance) spending, including spending related to dialysis services for their aligned ESRD beneficiaries. It is understood that some value-based healthcare models may also include Medicare Part D (e.g., prescription drug coverage) spending.

An integrated care system 220 may form a part of a clinical system for diagnosing and treating a patient in all aspects of care. The integrated care system 220 may be connectable to additional clinical systems, including but not limited to a pharmacy, a CKD/ESRD data registry, and the like. For example, the integrated care system may automatically send prescriptions and other patient information to a pharmacy based on information provided by a medical professional, and may be able to send and receive data and information to the CKD/ESRD data registry, for comparison to other patients and projections for future treatment. The integrated care system may determine events associated with CKD/ESRD and take appropriate action, including but not limited to informing patients, informing clinicians of when specific interventions are warranted, and/or alerting clinicians to upcoming important dates for interventions.

One or more outside, or external, systems may also be connectable to the integrated care system 220. For example, the external systems may include one or more of diagnostic and/or treatment equipment such as a dialysis machine, labs, doctor's office, hospital, and/or electronic medical records. Patient information may be sent and received between the integrated care system and the external systems, so that patient care may be more efficient, standardized, and consistent across several functions. For example, the integrated care system 220 (see FIG. 2A) may receive information from a patient's electronic medical records, thereby accessing historical information. A dialysis unit, or dialysis machine, doctor's office, labs, and hospitals may send and receive information to and from the integrated care system based on patient treatment.

As described below with respect to FIGS. 12-15, in some embodiments, a care coordination system may provide information to a dialysis machine 1200, 1300, 1400, for use in dialysis treatment. In some embodiments, the integrated care system may send the dialysis machine 1200, 1300, 1400, a prescription from a medical professional for a prescribed dialysis treatment, in which case the integrated care system may receive the prescription from a doctor's office or hospital. The integrated care system may also be able to verify the prescribed treatment against the patient's lab work or medical records, and in some instances may remotely program the prescription onto the patient's dialysis machine, or forward the prescription to the machine for local set-up. In this manner, the patient may be sure to receive the necessary and correct treatment and may be prevented from administering or receiving an improper amount of dialysis treatment, thereby reducing human error and improving patient care. The integrated care system 220 may also be able to inform the relevant medical professional based on information received from these external systems, as well as the additional clinical systems, e.g., to provide appropriate medical treatment to the patient, including course(s) of treatment that may lessen or avoid a risk of hospitalization, which may even alter a patient's disease progression. If a patient receives proactive medical treatment, the patient's kidney disease progression may be slowed and/or even reversed.

Figure 2B:
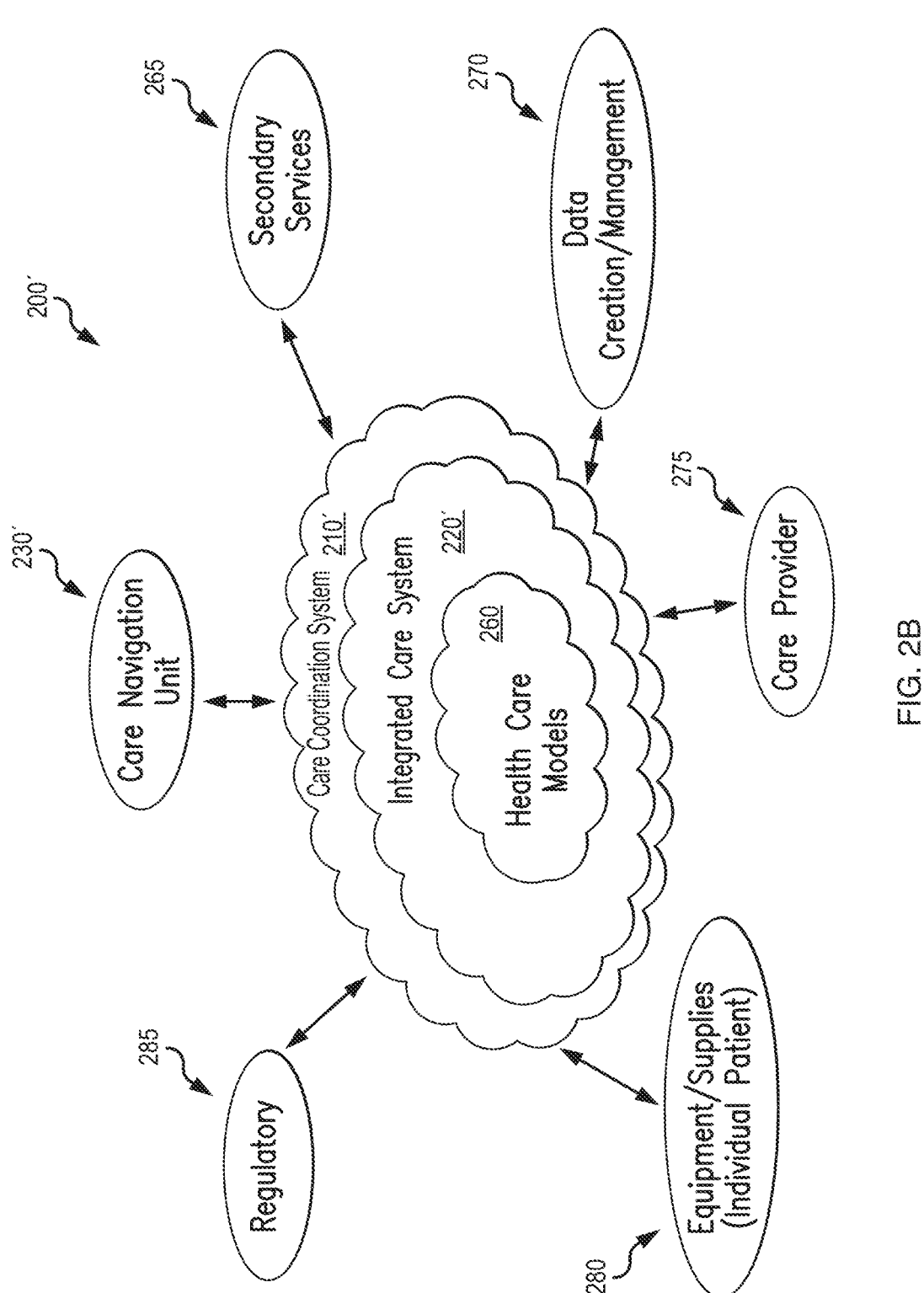
FIG. 2B is a diagram illustrating an exemplary embodiment of systems for assessing and treating disease, including kidney disease, in accordance with the present disclosure.

FIG. 2B is another illustration of a care coordination framework. Coordinated care framework 200' of FIG. 2B shares the features described herein with respect to coordinated care framework 200 of FIG. 2A except to the extent described otherwise. The coordinated care framework 200' described in this example is provided for integrating patient care in treating kidney disease, e.g., ESRD and/or CKD is shown (although it may be adapted as well for other chronic conditions similar to the framework of FIG. 2A). A care coordination system 210' may coordinate at least some aspects of a patient's care with the integrated care system 220' (which may include and execute healthcare-related models and/or programs 260), to support patient care. Various components may engage within the care coordination system 210' to provide complete patient care via the care framework. For example, any number of integrated care components may send and receive information to and from the integrated care system 220', including but not limited to a secondary services component 265, data creation and/or management component 270, care provider component 275, equipment and/or supplies component 280, and regulatory component 285. In some embodiments, the care coordination system 210' may engage with third party resources, including but not limited to lab services, research, etc. In some embodiments, the care framework may encompass, or is implemented by, or is associated with, a care navigation unit 230'. In the example of FIG. 2B, it is noted that the care navigation unit 230' is indicated as a separate entity from the care coordination system 210', but it should be understood that in other examples (see, e.g., FIG. 2A), the care navigation unit may be included as part of the care coordination system.

Figure 6:
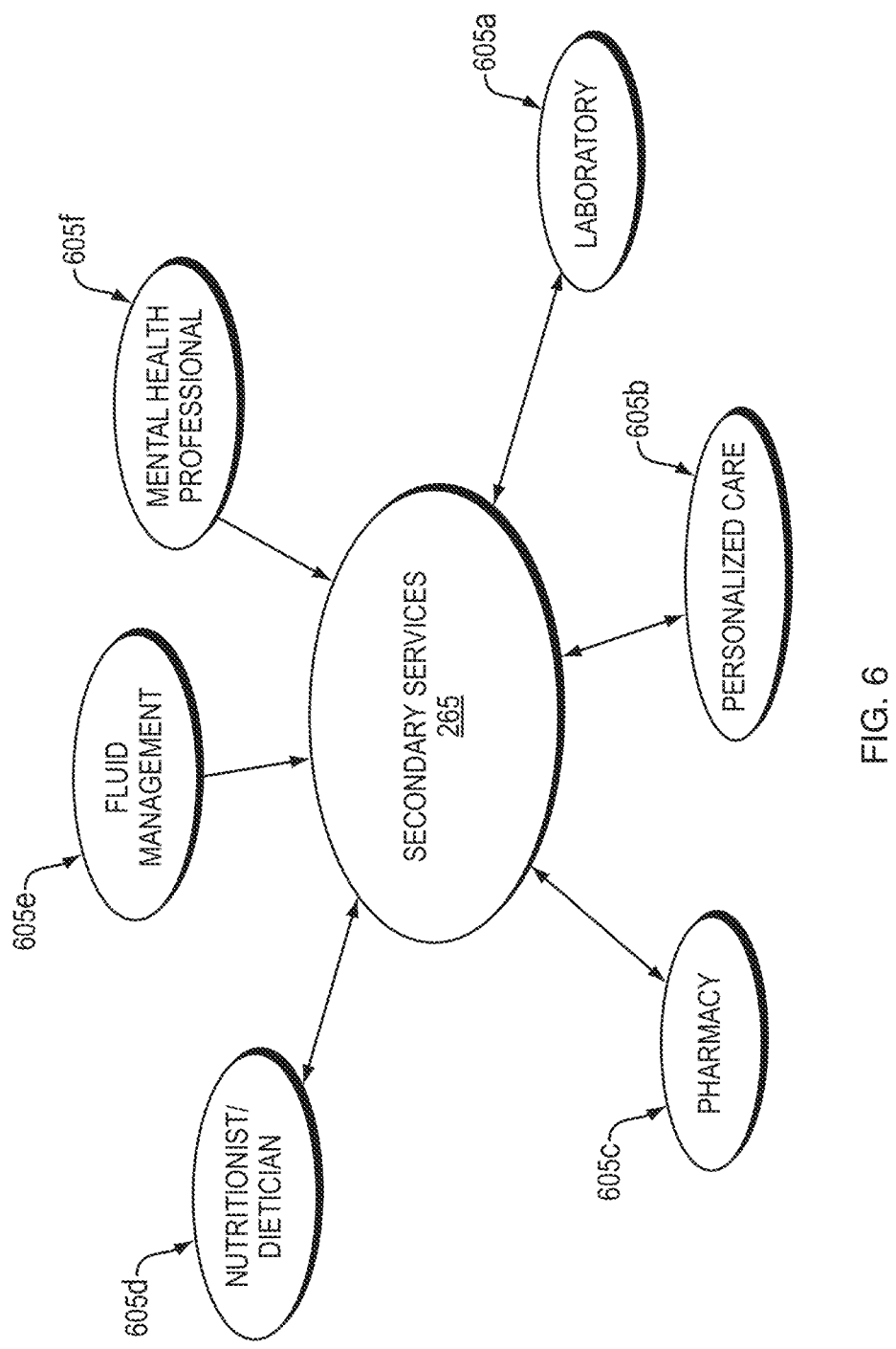
FIGS. 6-10 are diagrams illustrating exemplary embodiments of components of systems for providing coordinated healthcare, in accordance with the present disclosure.

Each component of an integrated care system (e.g., care analysis and guidance system) 220, 220' may include one or more units, including internal services and support as well as external services and support, as described above. As shown in FIG. 6, the secondary services component 265 may include any number "n" of services 605a, 605b, . . . 605n related to secondary patient services. For example, secondary services may include laboratory 605a, personalized care 605b, and/or pharmacy 605c. Each of the secondary services 605a, 605b, . . . 605n may send and receive patient information to the integrated care system 220, 220', for compilation and analysis. For example, a laboratory may automatically send results of patient bloodwork and other test results to the integrated care system 220, 220'. Additionally, the integrated care system 220, 220' may automatically send testing instructions to the laboratory for selected tests on patient samples, based on determinations from medical professionals, and/or other information gathered by the care coordination system 210' via a care framework. Similarly, the integrated care system 220, 220' may automatically send prescriptions and dosage instructions to a pharmacy based on a patient's test results and other factors determined by the integrated care system 220, 220'. The pharmacy may also send information to the integrated care system 220, 220' related to other patient prescriptions for potential adverse drug interactions, how timely a prescription is refilled, and/or patient interaction with the pharmacist, etc.

In some embodiments, a patient may benefit from care by a nutritionist and/or dietician 605d, to adjust to dietary restrictions as a component to their care. For example, ESRD patients may have prescribed dietary requirements are part of receiving hemodialysis and other treatment for their kidney disease. A patient may benefit from consultation with a nutritionist and/or dietician, for moving towards a healthier eating lifestyle and other potential health-related benefits. Fluid management 605e may also be managed for a patient, to ensure a patient is receiving proper amounts and types of fluid. Patients living with CKD and/or ESRD may have fluid restrictions for better dialysis outcomes. Some patients may have difficulty in understanding liquid intake, and/or may be unable to reliably track their fluid intake. In some embodiments, fluid management may be managed by a nutritionist and/or dietician, although it is understood that in other embodiments a patient's fluid intake may be managed by another medical professional. In embodiments, a patient may benefit from care by mental health professionals 605f, for example, psychologists, psychiatrists, and/or other counseling services. As described above, a patient's mental well-being may be affected by progression of an illness, and may otherwise be missed by other medical professionals in the course of treatment. As such, scheduling and providing access to mental health professionals may improve the patient's total health.

Figure 7:
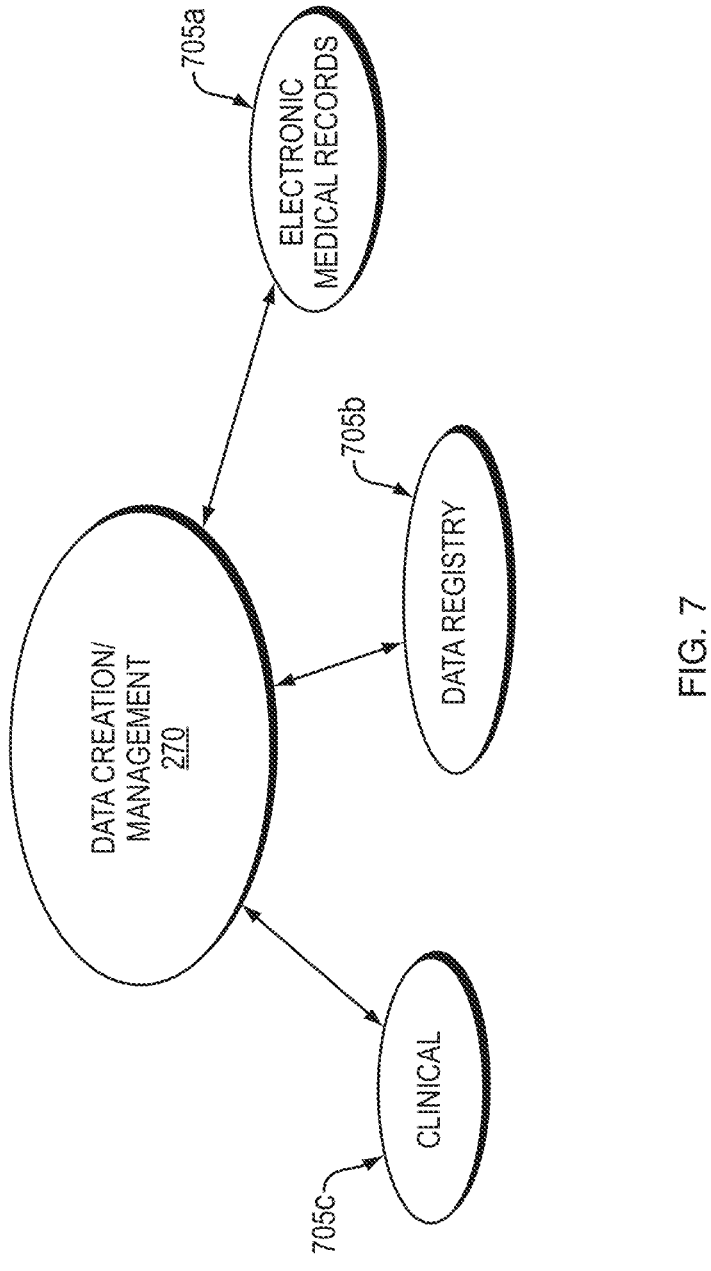

Referring now to FIG. 7, the data creation/management component 270 may include one or more units related to the creation and/or management of patient data, including internal services and support as well as external services and support, as described above. For example, the data creation/management component 270 may include any number "n" of services 705a, 705b, . . . 705n. As shown in FIG. 7, electronic medical records (EMR) 705a, data registry 705b, and clinical information 705c, may receive, store, and/or send patient data records as determined by the care analysis and guidance system 220, 220'. For example, a patient's medical records may be automatically updated after receiving lab results, treatment information, and/or notes from medical professionals. The care analysis and guidance system 220, 220' may utilize a patient's medical records for trends or triggering events, so that the care coordination system 210' may provide relevant information to a medical professional for treatment and other care option recommendations and timing and coordination of various types of possible interventions. In some embodiments, the care analysis and guidance system 220, 220' may analyze multiple patients as part of a data registry, for determining global trends and analyzing data from a macro-level.

Figure 8:
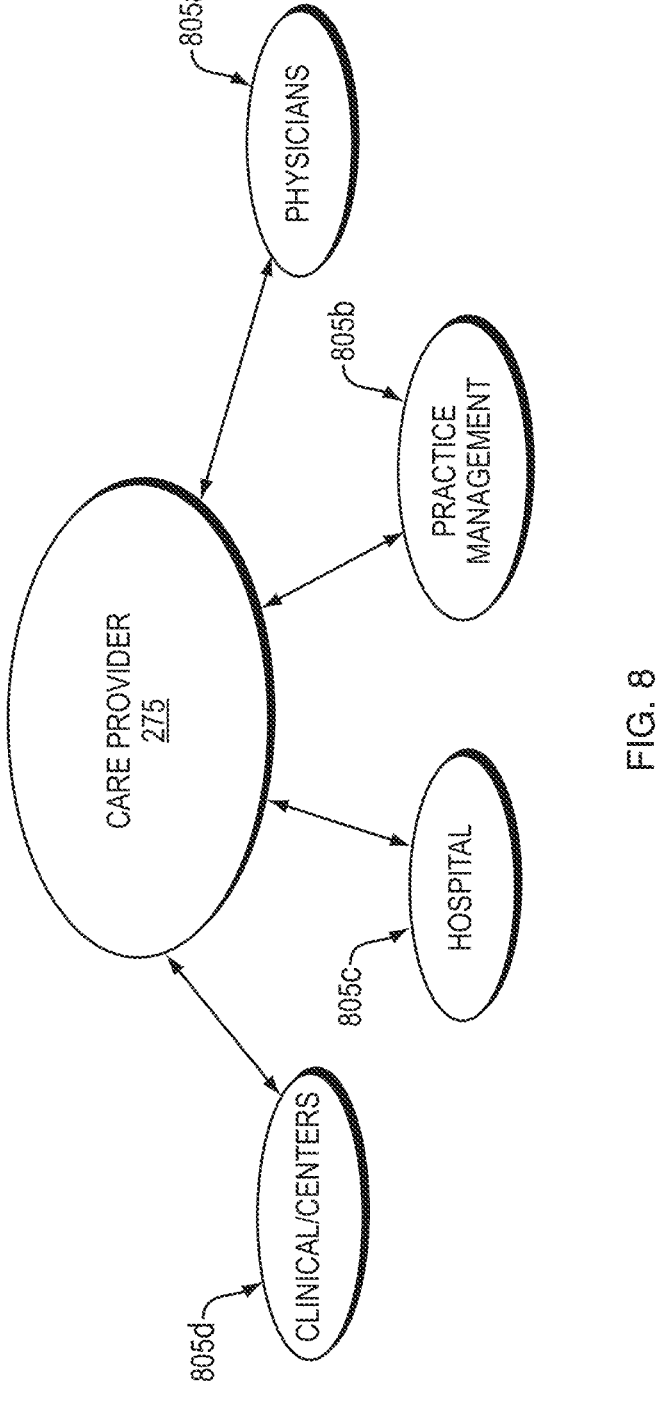

FIG. 8 shows an exemplary care provider component 275, including one or more units which provide patient care, as indicated by reference numerals 805a, 805b, . . . 805n. Any number "n" of units may be included in the provider component 275. In some embodiments, care providers may include physicians and/or physician groups 805a (e.g., primary care physicians (PCP) and specialists such as nephrologists), practice management systems 805b, hospitals 805c, and/or clinic/centers 805d, although additional or alternative care providers may also be envisioned. The integrated care system 220, 220' may send and receive information to and from the care providers for patient treatment. For example, the integrated care system 220, 220' may receive physician notes of patient examinations, hospitalization information, and the like, and may send calculated information and other determined factors based on other patient data received. For example, the integrated care system 220, 220' may send estimations and treatment recommendations to identify, reduce, avoid, and/or eliminate patient risk of aspects and/or effects of renal disease or renal disease treatments for providing treatment to a patient based on all received patient data and assessments performed thereon.

Figure 9:
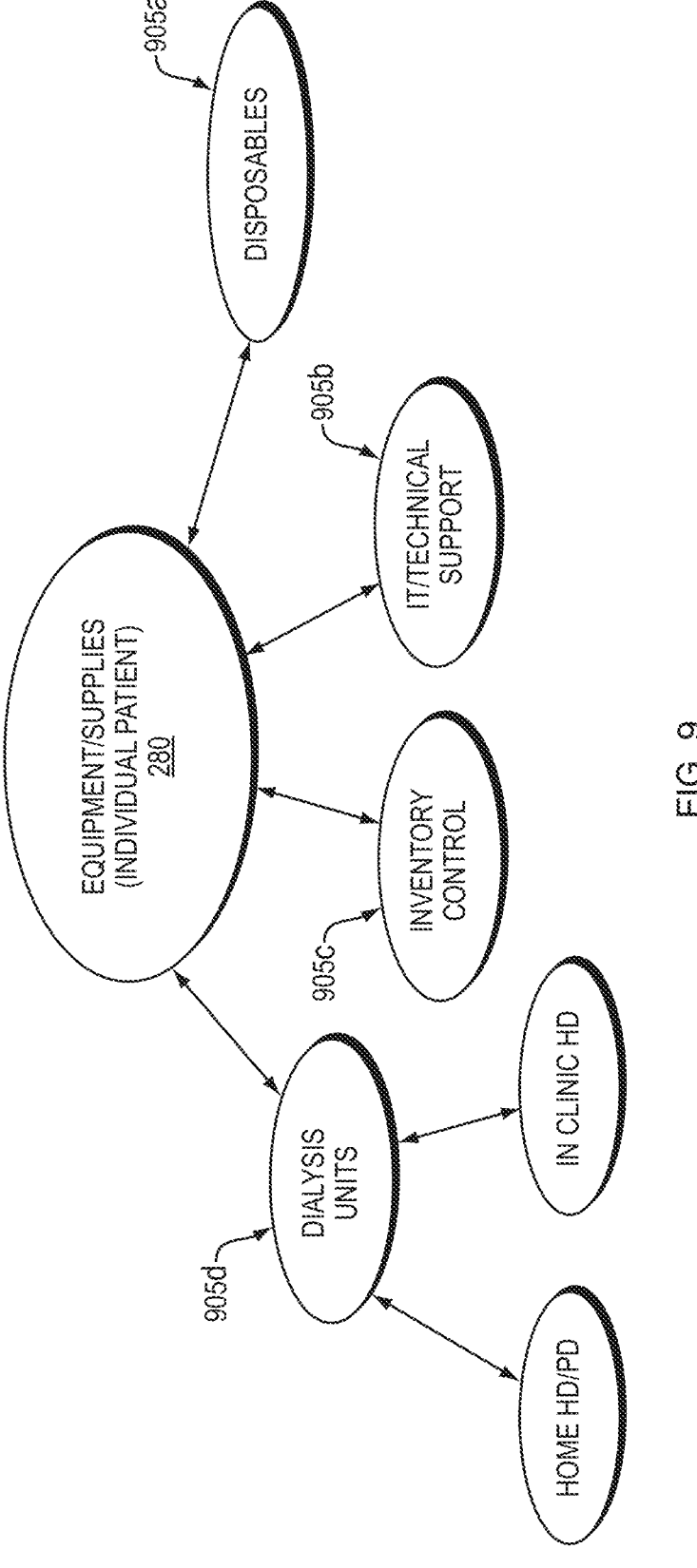

FIG. 9 shows an exemplary equipment and/or supplies component 280, for example, treatment supplies, for an individual patient, which may include any number "n" of services 905*a*, 905*b*, . . . 905*n*. In some embodiments, the integrated care system 220, 220' may send and receive information related to disposable medical equipment 905*a*, information technology (IT) technical support 905*b*, inventory control 905*c*, and/or dialysis units 905*d* or suite of dialysis machines in a clinic. As described above, many patients receive treatment at home, such as home dialysis, requiring an ongoing supply of disposable medical supplies for each treatment. Deliveries of supplies and/or dialysis equipment may be automatically monitored, replenished, and/or inventoried by the integrated care system 220, 220', to ensure proper machine functioning and a steady supply of materials and resources to ensure a patient receives all prescribed treatments.

Figure 10:
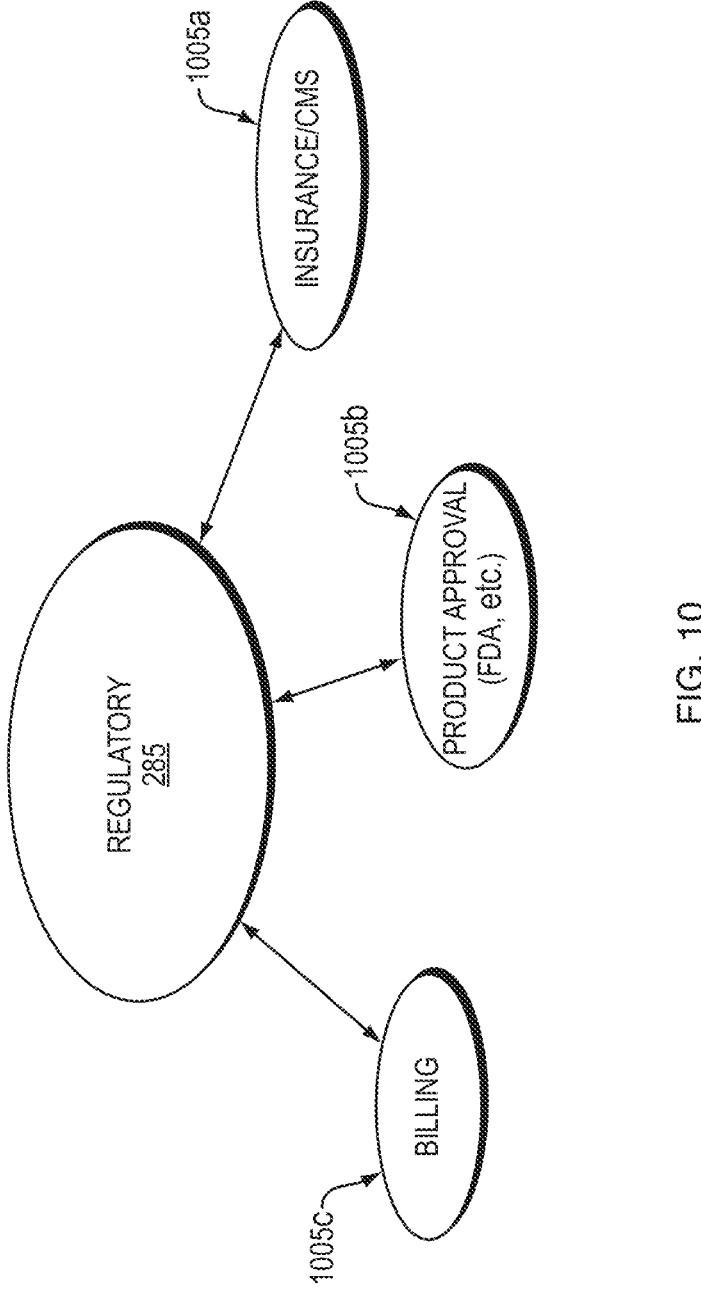

FIG. 10 shows an exemplary regulatory component 285, which may include any number "n" of services 1005*a*, 1005*b*, . . . 1005*n* related to governmental and regulatory requirements. For example, certain state and federal regulations and regulatory authorities may be involved in insurance and/or Centers for Medicaid and Medicare Services (CMS) 1005*a*, product approvals for the public (e.g., the Food and Drug Administration (FDA)) 1005*b*, and billing 1005*c*. The integrated care system 220, 220' may send and receive information to and from each of these units to ensure correct billing coding, regulatory approvals, and/or insurance payments.

Figure 11:
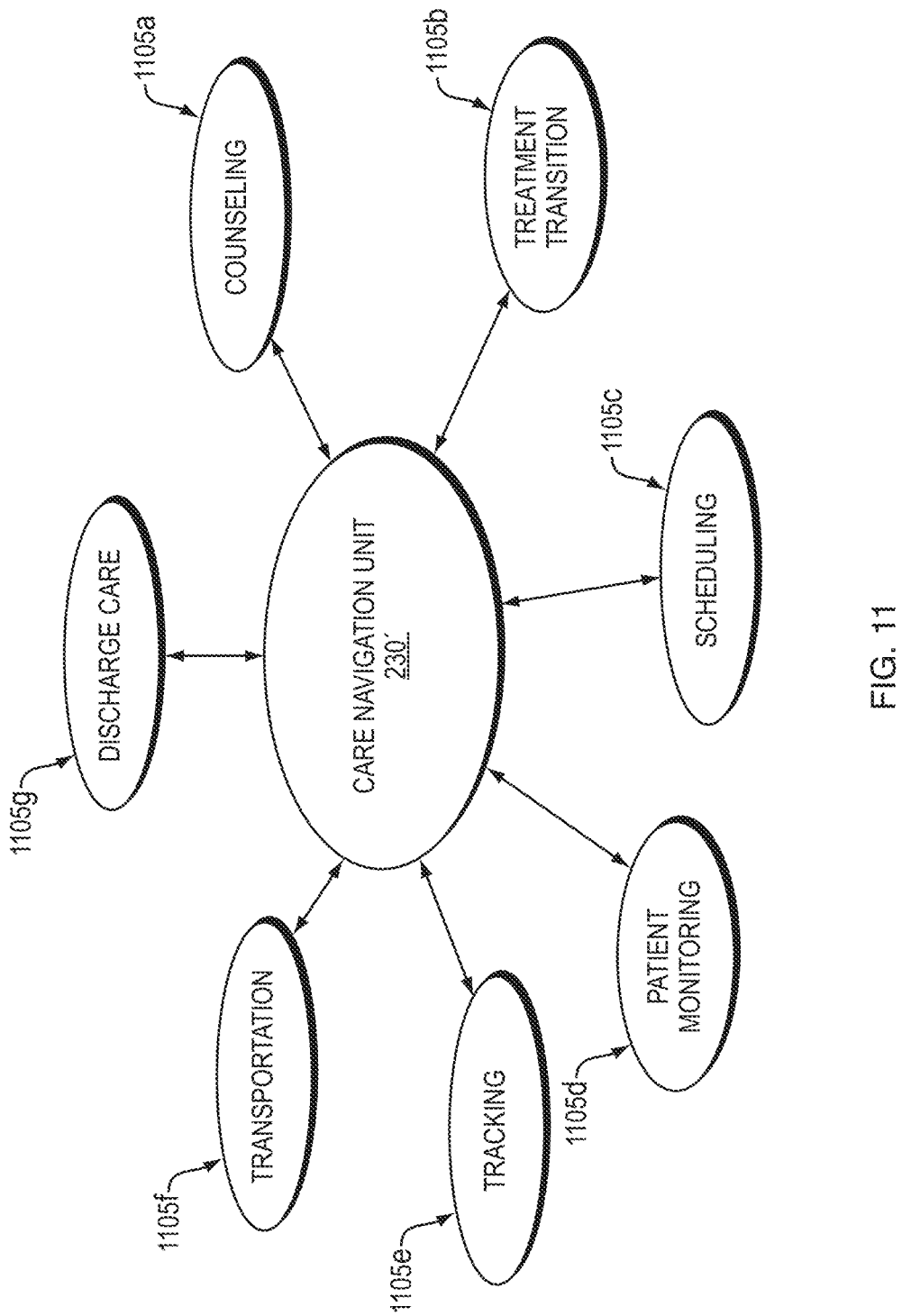
FIG. 11 is a diagram illustrating exemplary embodiments of care coordination components of systems providing coordinated healthcare, in accordance with the present disclosure.

A care navigation unit 230, 230', as introduced above, may oversee and coordinate patient care based on analysis and calculations by the integrated care system 220, 220' determined from data and information from any of the components 265, 270, 275, 280, 285, as well as the care coordination system 210'. For example, a care navigation unit 230', may coordinate care to patients to follow through on interventional treatments to address functional and/or cognitive patient impairment over time, improve comorbidity management, and help drive high-value care options and timing of treatment decisions to patients over time. As shown in FIG. 11, care navigation unit 230, 230' may include different aspects of health care coordination as indicated by reference numerals 1105*a*, 1105*b*, . . . 1105*n*, including but not limited to counseling, treatment transition, scheduling, patient monitoring, tracking, transportation, and/or discharge care. For example, the integrated care system 220, 220' may determine that a patient requires transportation to/from a treatment center, and may automatically schedule transportation, e.g., public transportation, carpool, taxi, ride share, etc., so that the patient may not miss a scheduled treatment. Additionally, the integrated care system 220, 220' may send patient results to the relevant care providers, e.g., medical specialists, doctors, and/or nurses, for monitoring and/or treatment recommendations. Care navigation unit 230' may provide services to patients addressing their complete healthcare needs related to their kidney disease.

The care navigation unit 230, 230' may include treatment transition 1105*b*, for an integrated care system 220, 220' to coordinate patient care through progression of kidney disease. For example, a patient may initially be diagnosed with chronic kidney disease (CKD). Over time however, without interventional treatment (e.g., a kidney transplant) or improved kidney function, the patient may progress to end-stage renal disease (ESRD). As the patient's kidney disease progresses, the patient may need additional services, support, and/or health care, which may be overseen and/or managed under the care framework 200' by the care navigation unit 230' via the integrated care system 220, 220' and through a care framework of care coordination system 210, 210'. As described above, the care navigation unit 230, 230' may provide additional services and/or treatments through the care framework to a patient based on the associated hospitalization risk score. For example, to reduce a risk of hospitalization, the care navigation unit 230, 230' may assess the patient's condition (see e.g., FIGS. 1D-1F) based on patient parameters provided to the integrated care system 220, 220'. The care navigation unit 230, 230' may then determine interventional treatment, if necessary, to lower the hospitalization risk score. By proactively addressing potential patient health concerns, a hospitalization stay may be delayed and/or avoided, and a patient's disease progression may be slowed or reversed.

Figure 3:
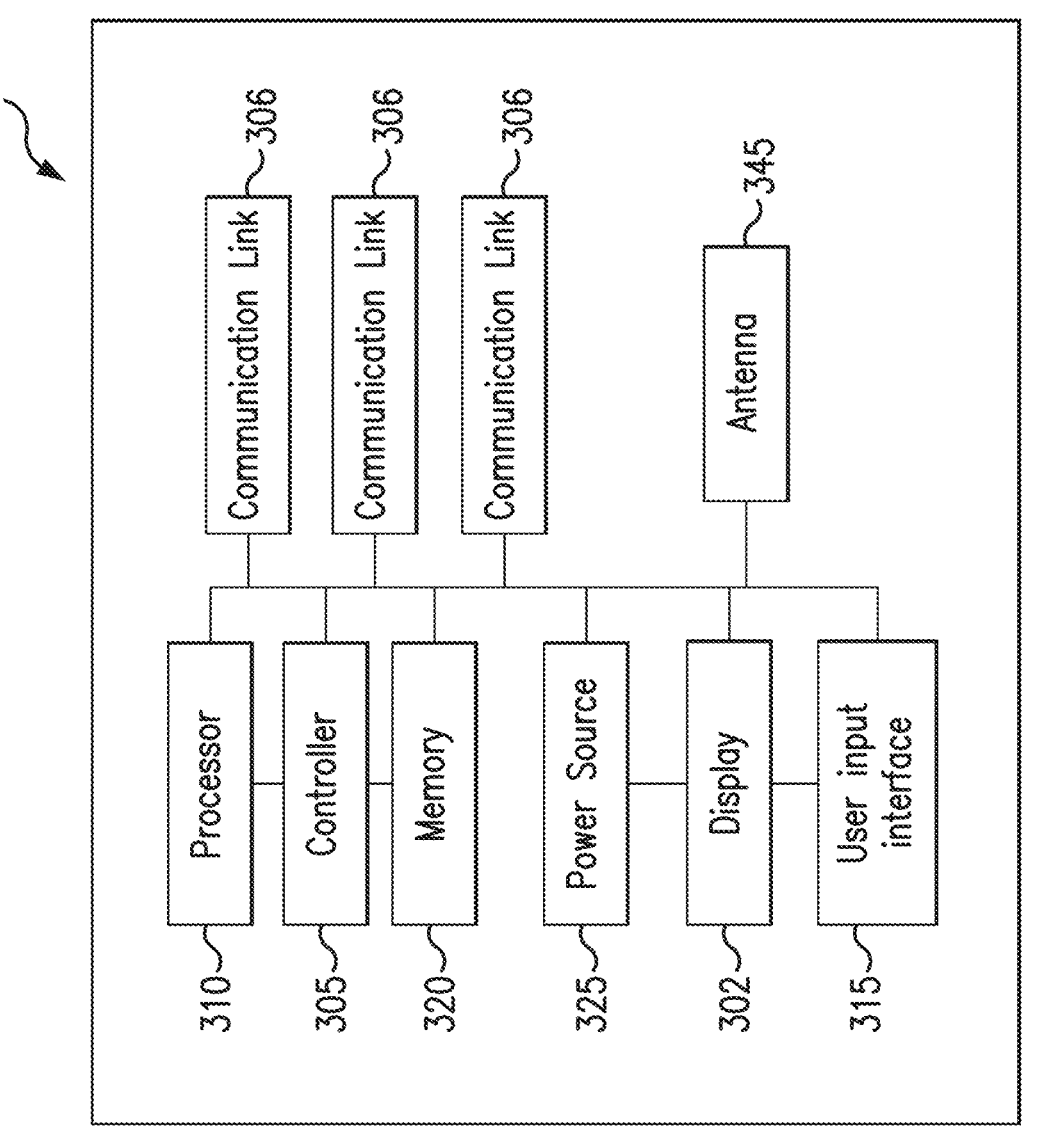
FIG. 3 is a block diagram illustrating an exemplary embodiment of an integrated care system in accordance with the present disclosure.

Referring now to FIG. 3, an integrated care system, such as integrated care system 220, 220', may include a controller 305, a processor 310, and a memory 320. The controller 305 may automatically control signals received and sent to other systems, e.g., the additional clinical systems, the external systems, and the practice management and billing system. Communication between the controller 305 and other systems may be bi-directional, whereby the systems may acknowledge control signals, and/or may provide information associated with the system and/or requested operations. Additionally, a user input interface 315 and display 302 may be disposed to receive and/or display input from a user, e.g., a patient or a medical professional such as a doctor, nurse, technician, or the like. Examples of the components that may be employed within the user input interface 315 include keypads, buttons, microphones, touch screens, gesture recognition devices, display screens, and speakers. In some embodiments, the integrated care system 220, 220' may be a server, a computer, or other device for storing and processing data, and controlling signals to other systems. A power source 325 may allow the integrated care system 220, 220' to receive power, and in some embodiments may be an independent power source.

The processor 310 may be configured to execute an operating system, which may provide platform services to application software, e.g., for operating the integrated care system 220, 220'. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux. According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, data records, timing for treatment and/or operations, historic information, statistical information, and informational databases for treatments. A database may be stored in the memory 320 of the integrated care system 220, 220', and may be accessible by the processor 310 and controller 305. For example, historical data of patient information may be extracted from various databases in the integrated system 220, 220', including but not limited to patient lab results, treatment data, technician data during treatment (nurse notes), etc. Extracted data may be used to generate a database which may be used to train a machine learning model, to assess factors leading to a patient's hospitalization. For example, a machine learning model may identify patients who have been hospitalized and analyze patient lab results, treatment data, nurse notes, and the like, for commonalities that may have led to the hospitalization. The medium may, for example, be an optical disk, magnetic disk or flash memory, among others, and may be permanently affixed to, or removable from, the controller 305.

The integrated care system 220, 220' may include communication links 306, so that other systems may be connectable to the integrated care system 220, 220'. For example, additional clinical systems, external systems, and practice management and billing systems, may be connectable to the integrated care system 220, 220' to send and receive data and information associated with providing patient care. In some embodiments, the communication links 306 may be wireless, so that the systems may be remote, or the integrated care system 220, 220' and/or one or more of the systems 265, 270, 275, 280, 285, 230' may reside and operate in a cloud-based architecture.

One or more algorithms may utilize the model of historical data, to analyze current patient data as it is entered and/or gathered by the integrated care system 220, 220'. Algorithms may analyze the patient data based on the historical data to determine patients most likely to be hospitalized. The integrated care system 220, 220' may further generate reports identifying patients determined to be most likely at risk for hospitalization. Such reports may be sent to the care coordination unit 125, for follow up and treatment recommendations (see FIGS. 1A-1F). This may allow medical professionals time to intervene and address potential escalating health concerns with patients, which may ultimately lower or avoid the hospitalization risk. Timely intervention may slow or even reverse a patient's kidney disease progression.

The integrated care system 220, 220' may also be wirelessly connectable via an antenna 345 for remote communication. For example, the integrated care system 220, 220' may determine one or more patient parameters by the controller 305, processor 310, and/or memory 320, and may access other patient parameters being stored by an outside system, e.g., in electronic medical records stored on a server or database in a location remote from the system or machine, or from labs or hospital information. It may be advantageous for the integrated care system 220, 220' to access other patient parameters that may otherwise be unknown or undeterminable in order to provide a complete care analysis of the patient. As described above, patient data may be sent to and/or accessible by the integrated care system 220, 220'. The controller 305, processor 310, and memory 320 may receive, store, and/or determine relevant demographic and laboratory values, or other data, for calculations. The integrated care system 220, 220' may then use the calculations for determining a risk of hospitalization. In some embodiments, as patient parameter information is updated, e.g., new data points may be included in the system, and corresponding future or identified patient parameters may be updated and adjusted accordingly. In embodiments, any number of variables may be extracted for determining a patient risk of hospitalization, e.g., imminent hospitalization, or hospitalization within one week or some other defined window of time. In some embodiments, the integrated care system 220, 220' may utilize patient variables for determining long-term hospitalization risks, e.g., within the next twelve months. Additionally, notes, e.g., notes from medical professionals, may be included in determining patient risk of hospitalization. The one or more algorithms may generate a risk score of hospitalization based on the extracted variables and the historical data, and in some embodiments may identify leading factors related to the generated risk score. As described above, by determining a patient's risk and reasons for hospitalization, medical professionals may be able to develop individualized patient interventions to reduce risk and/or prevent hospitalization.

Figure 4:
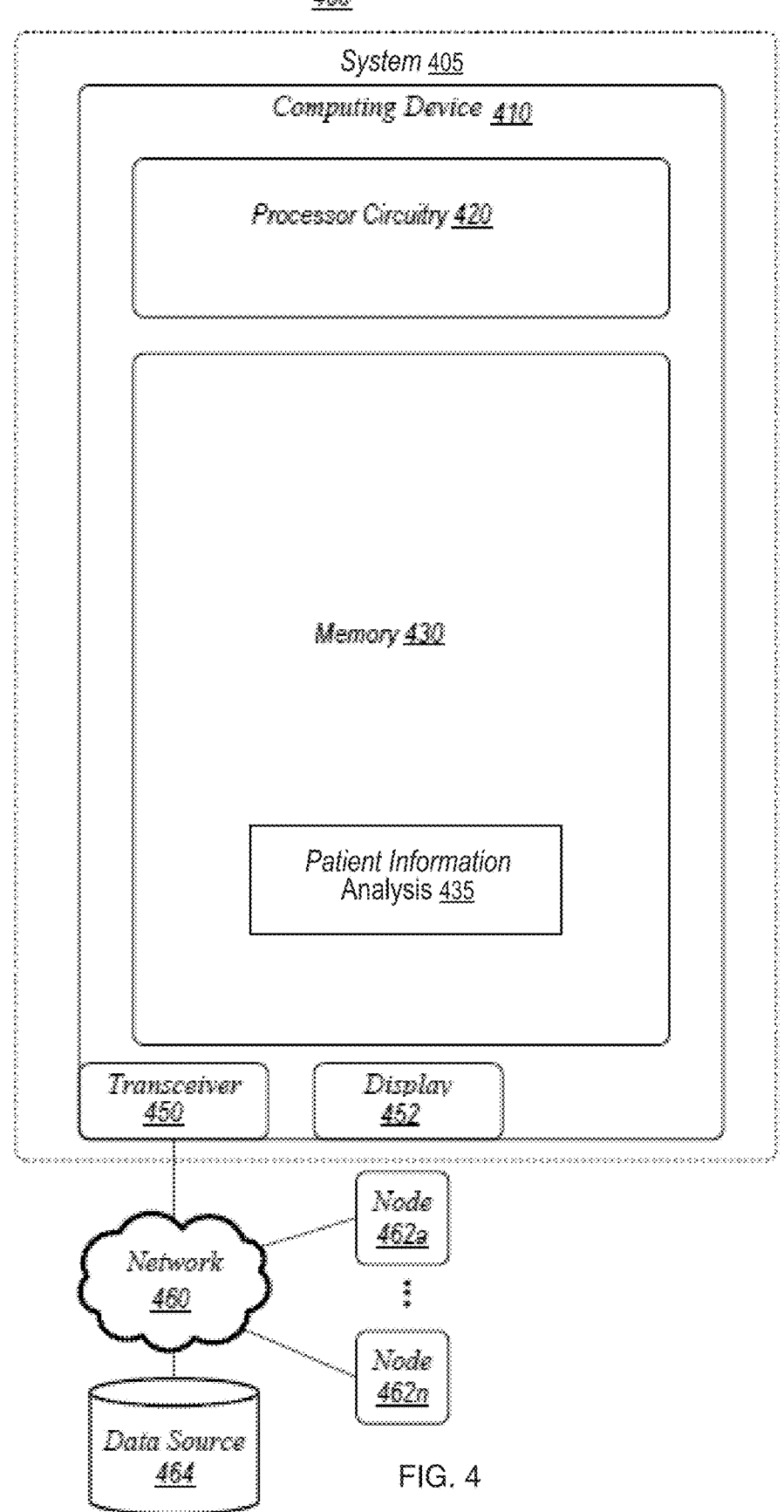
FIG. 4 is a block diagram illustrating an exemplary embodiment of an operating environment in accordance with the present disclosure.
Figure 5:
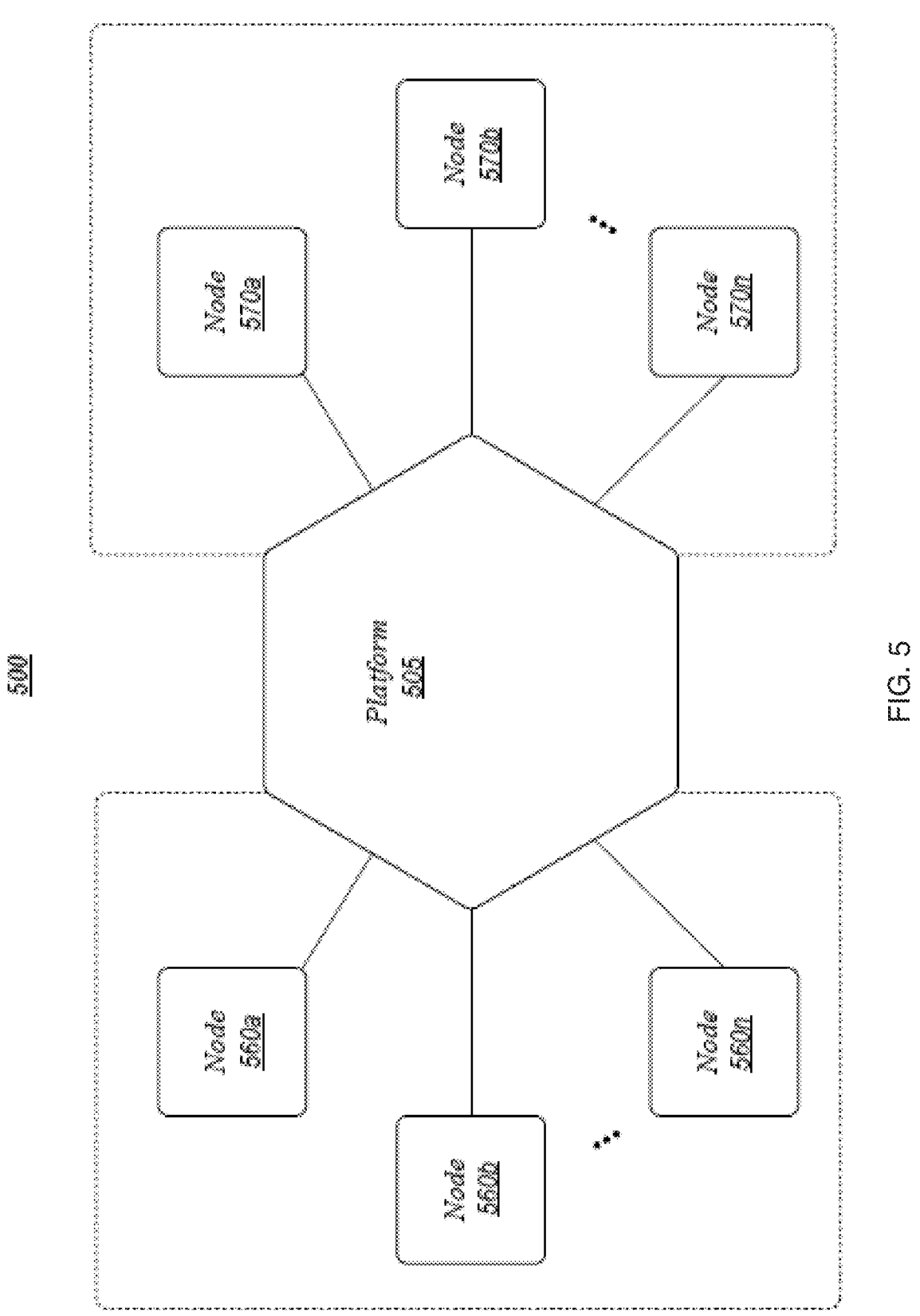
FIG. 5 is a block diagram illustrating an exemplary embodiment of another operating environment in accordance with the present disclosure.

Referring now to FIGS. 4-5, exemplary embodiments of an operating environment for a healthcare system (e.g., coordinated care framework 200, 200'), including integrated care system (care analysis and guidance system) 220, 220', are described. FIG. 4 illustrates an example of an operating environment 400 that may be representative of some embodiments. As shown in FIG. 4, operating environment 400 may include a system 405 operative for treating patients, e.g., patients having chronic illnesses. In various embodiments, the system 405 may include computing device 410. Computing device 410 may include processing circuitry 420, a memory unit 430, a transceiver 450, and/or a display 452. Processing circuitry 420 may be communicatively coupled to memory unit 430, transceiver 450, and/or display 452. It is understood that in some embodiments, system 405 may include the coordinated care framework 200, 200', and in some embodiments, the system 405 may include other systems and/or frameworks.

In some embodiments, computing device 410 may be connected to network 460 through transceiver 450. Network 460 may include nodes 462a-n, for example, remote computing devices, data sources 464, and/or the like.

Processing circuitry 420 may include and/or may access various logic for performing processes according to some embodiments. Processing circuitry 120, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1500 of FIG. 15. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

It is also understood that components of the processing circuitry 420 may be located within an accelerator, a processor core, an interface, an individual processor die, implemented entirely as a software application and/or the like.

Memory unit 430 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 430 may store various information, e.g., one or more programs, to perform various functions identifying and treating patients with CKD and/or ESRD. In some embodiments, the memory 430 may include logic having application programming interfaces (APIs) and/or graphical user interfaces (GUIs) to read, write, and/or otherwise access information, such as via display 452, web interfaces, mobile application ("mobile applications," "mobile apps," or "apps"), and/or the like. In this manner, in some embodiments, an operator may search, visualize, read, add to, or otherwise access information associated with a patient population for identifying and treating CKD and/or ESRD.

In some embodiments, memory unit 430 may store various information associated with a patient population for identifying and treating CKD and/or ESRD. In some embodiments, information stored in memory unit 430 may be retrieved from and/or moved into a data source 464 including, without limitation, a hospital information management system (HIMS), laboratory information management system (LIMS), Health Information System (HIS), electronic medical records (EMR), a clinical trial database, and/or the like. For example, one or more programs or algorithms, or combinations thereof, as a patient information analysis 435, may be implementable. In some embodiments, the programs and/or algorithms may be utilized for determining a risk score of hospitalization.

FIG. 5 illustrates an example of an operating environment 500 that may be representative of some embodiments. As shown in FIG. 5, operating environment 500 may include a platform 505, e.g., a healthcare exchange platform. In some embodiments, the platform 505 may be operative to provide for the exchange of clinical data and/or clinical trial information among interested entities. In various embodiments, the platform 505 may include an application platform operative for identifying a patient population and treating CKD and/or ESRD with services among nodes 560a-n and 570a-n. In exemplary embodiments, the platform 505 may be a software platform, suite, set of protocols, and/or the like provided to customers by a manufacturer and/or developer ("developer") associated with medical devices, medical care services, clinical research services, laboratory services, clinical trial services, and/or the like.

For example, a developer may provide the platform 505 as a data exchange interface for use by various entities, including government entities (for example, the FDA), and other stakeholders (for instance, pharmaceutical manufacturers, medical device manufacturers, and/or the like). An entity, such as a hospital, dialysis clinic, healthcare provider, government entity, regulatory entity, pharmaceutical manufacturer, medical device manufacturer, and/or the like providing and/or receiving clinical trial services via a node 570a-n provided by developer may use the platform 505 to implement processes according to some embodiments. Other entities may access the platform 505 via a GUI, such as a client application, web interface, mobile app, and/or the like, e.g., for performing functions associated with the memory 522. In some embodiments, at least a portion of the platform 505 may be hosted in a cloud computing environment.

Nodes 570a-n may be data producers for the memory 522 and nodes 560a-n may be data consumers of the memory 522. For example, node 570a-n may include entities providing clinical data, model information, and/or the like used by the memory 522 to generate, perform, and/or evaluate a patient population. Nodes 560a-n may include third-party applications, decision makers, analysis processes, regulators, and/or other data consumers that may be interested in the results of generating, performing, and/or evaluating the patient population. An entity may be both a data producer and a data consumer.

For example, node 560a may be care provider (node 560b) to provide treatment to a patient based on analysis of a patient population including medical records, laboratory data, pharmacy, and the like. (node 570a). Data producers 570a-n may provide analytical data, according to permissions, to the platform 505, for example, in the form of records in a HIMS, LIMS, EMR, and/or the like. Data consumers 560a-n may access analytical data, according to permissions, via the platform 505 (for example, through HIMS, LIMS, EMR, and/or the like and/or local copies of such records).

In some embodiments, the platform 505 may operate according to a cloud-based model and/or an "as-a-Service" model. In this manner, the platform 505 may provide for a service that operates as a single, central platform that allows entities to access clinical data, model information, simulation results, and/or the like.

Figure 12:
FIG. 12 is a schematic illustrating an exemplary embodiment of a dialysis machine in accordance with the present disclosure are shown.

In some embodiments, one of the recommended treatments and/or services may be to alter or change a dialysis treatment prescription for a patient. As illustrated in FIGS. 12-14 and described below, a dialysis machine 1200, 1300, 1400, e.g., a dialysis machine such as a peritoneal dialysis machine or a hemodialysis machine, may be connected to the integrated care system 220, 220' for sending and receiving dialysis information to provide appropriate care to a patient. The hemodialysis machine may be located in a renal clinic, such as a kidney care clinic, dialysis clinic, or other third-party care provider. In some embodiments, the peritoneal dialysis machine and/or the hemodialysis machine may be home machines, e.g., treatment may be administered in a patient's home. As described above, an integrated care system may be applicable to other chronic illnesses, and may be connected to machines related to those illnesses, including but not limited to chronic kidney disease, or one or more of the other chronic diseases and conditions mentioned above. For example, the machine 1200, 1300, 1400 may send patient data to the integrated care system 220, 220', for use in the one or more algorithms as data for extraction and/or processing for determining whether an ESRD patient is at risk for hospitalization.

Referring to FIG. 12, a schematic of an exemplary embodiment of a dialysis machine 1200, and a controller 1205 in accordance with the present disclosure are shown. The machine 1200 may be a dialysis machine, e.g., a peritoneal dialysis machine or a hemodialysis machine, for performing a dialysis treatment on a patient (see FIGS. 12-14). The controller 1205 may automatically control execution of a treatment function during a course of dialysis treatment. For example, the controller 1200 may control dialysis treatment based on information received from the care analysis and guidance system 220, 220'. The controller 1205 may be operatively connected to sensors 1240 and deliver one or more signals to execute one or more treatment functions, or a course of treatment associated with various treatment systems. Although FIG. 12 illustrates the components integrated into the dialysis machine 1200, at least one of the controller 1205, processor 1210, and memory 1220 may be configured to be external and wired or wirelessly connected to the dialysis machine 1200, as an individual component of a dialysis system. In some embodiments the controller 1205, processor 1210 and memory 1220 may be remote to the dialysis machine and configured to communicate wirelessly.

In some embodiments, the controller 1205, processor 1210, and memory 1220 of the system or machine 1200, 1300, 1400, may receive signals from sensor 1240 indicating one or more patient parameters. Communication between the controller 1205 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

The dialysis system or machine 1200, 1300, 1400, may also include at least one pump 1250 operatively connected to the controller 1205. The controller 1205 may also be operatively connected to one or more speakers 1230 and one or more microphones 1235 disposed in the system or machine 1200, 1300, 1400. The user input interface 1215 may include a combination of hardware and software components that allow the controller 1205 to communicate with an external entity, such as a patient or other user. These components may be configured to receive information from actions such as physical movement or gestures and verbal intonation. In embodiments, the components of the user input interface 1215 may provide information to external entities. Examples of the components that may be employed within the user input interface 1215 include keypads, buttons, microphones, touch screens, gesture recognition devices, display screens, and speakers.

As shown in FIG. 12, sensors 1240 may be included for detecting and monitoring one or more parameters and be operatively connected to at least the controller 1205, processor 1210, and memory 1220. The processor 1210 may be configured to execute an operating system, which may provide platform services to application software, e.g., for operating the dialysis machine 1200. These platform services may include inter-process and network communication, file system management and standard database manipulation. One or more of many operating systems may be used, and examples are not limited to any particular operating system or operating system characteristic. In some examples, the processor 1210 may be configured to execute a real-time operating system (RTOS), such as RTLinux, or a non-real time operating system, such as BSD or GNU/ Linux. According to a variety of examples, the processor 1210 may be a commercially available processor such as a processor manufactured by INTEL, AMD, MOTOROLA, and FREESCALE. However, the processor 1210 may be any type of processor, multiprocessor or controller, whether commercially available or specially manufactured. For instance, according to one example, the processor 1210 may include an MPC823 microprocessor manufactured by MOTOROLA.

The memory 1220 may include a computer readable and writeable nonvolatile data storage medium configured to store non-transitory instructions and data. In addition, the memory 1220 may include a processor memory that stores data during operation of the processor 1210. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 1220 may include executable programs or other code that may be executed by the processor 1210. The instructions may be persistently stored as encoded signals, and the instructions may cause the processor 1210 to perform the functions described herein. The memory 1220 may include information that is recorded, on or in, the medium, and this information may be processed by the processor 1210 during execution of instructions. The memory 1220 may also include, for example, specification of data records for user timing requirements, timing for treatment and/or operations, historic sensor information, and other databases and the like. The medium may, for example, be optical disk, magnetic disk or flash memory, among others, and may be permanently affixed to, or removable from, the controller 1200.

A pressure sensor may be included for monitoring fluid pressure of the system or machine 1200, 1300, 1400, although the sensors 1240 may also include any of a heart rate sensor, a respiration sensor, a temperature sensor, a weight sensor, a video sensor, a thermal imaging sensor, an electroencephalogram sensor, a motion sensor, audio sensor, an accelerometer, or capacitance sensor. It is appreciated that the sensors 1240 may include sensors with varying sampling rates, including wireless sensors. Based on data monitored by the sensors 1240, patient parameters such as a heart rate and a respiration rate may be determined by the controller 1200.

The controller 1205 may be disposed in the machine 1200, 1300, 1400, or may be coupled to the machine 1200, 1300, 1400, via a communication port or wireless communication links, shown schematically as communication element 1206. For example, the communication element 1206 may connect the dialysis machine 1200, 1300, 1400, to the care analysis and guidance system 220, 220', or another remote system such as an outside system or other clinical system. The dialysis machine 1200, 1300, 1400, may be connectable to the integrated care system 220, 220' via the communication element 1206 so that the controller 1205 may send and receive information and other signals to the care analysis and guidance system 220, 220'. As described above, the care analysis and guidance system 220, 220' may direct a prescribed dialysis treatment based on information received from other systems, e.g., outside systems, clinical systems, directly to the dialysis machine to ensure a patient receives the proper treatment. The dialysis machine may also send data and other information to the care analysis and guidance system 220, 220' so that if dialysis treatment requires adjustment, the care analysis and guidance system 220, 220' may ensure any changes will not adversely affect patient health.

As a component disposed within the machine 1200, 1300, 1400, the controller 1205 may be operatively connected to any one or more of the sensors 1240, pump 1250, pump heads 1404, 1406, and the like. The controller 1205 may communicate control signals or triggering voltages to the components of the system or machine 1200, 1300, 1400. As discussed, exemplary embodiments of the controller 1205 may include wireless communication interfaces. The controller 1205 may detect remote devices to determine if any remote sensors are available to augment any sensor data being used to evaluate the patient.

Figure 13A:
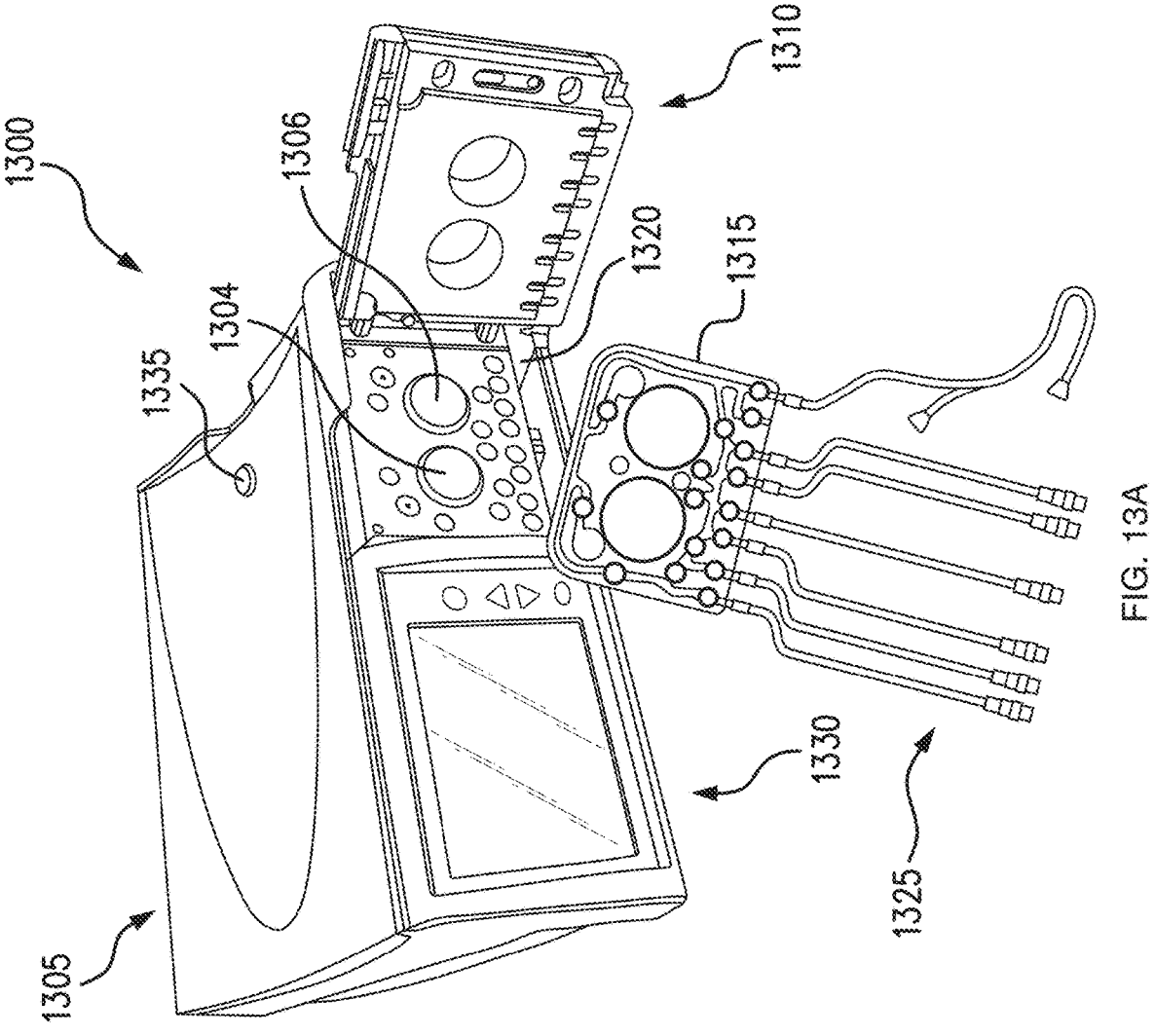
FIGS. 13A-13B illustrate an exemplary embodiment of a dialysis system in accordance with the present disclosure.
Figure 13B:
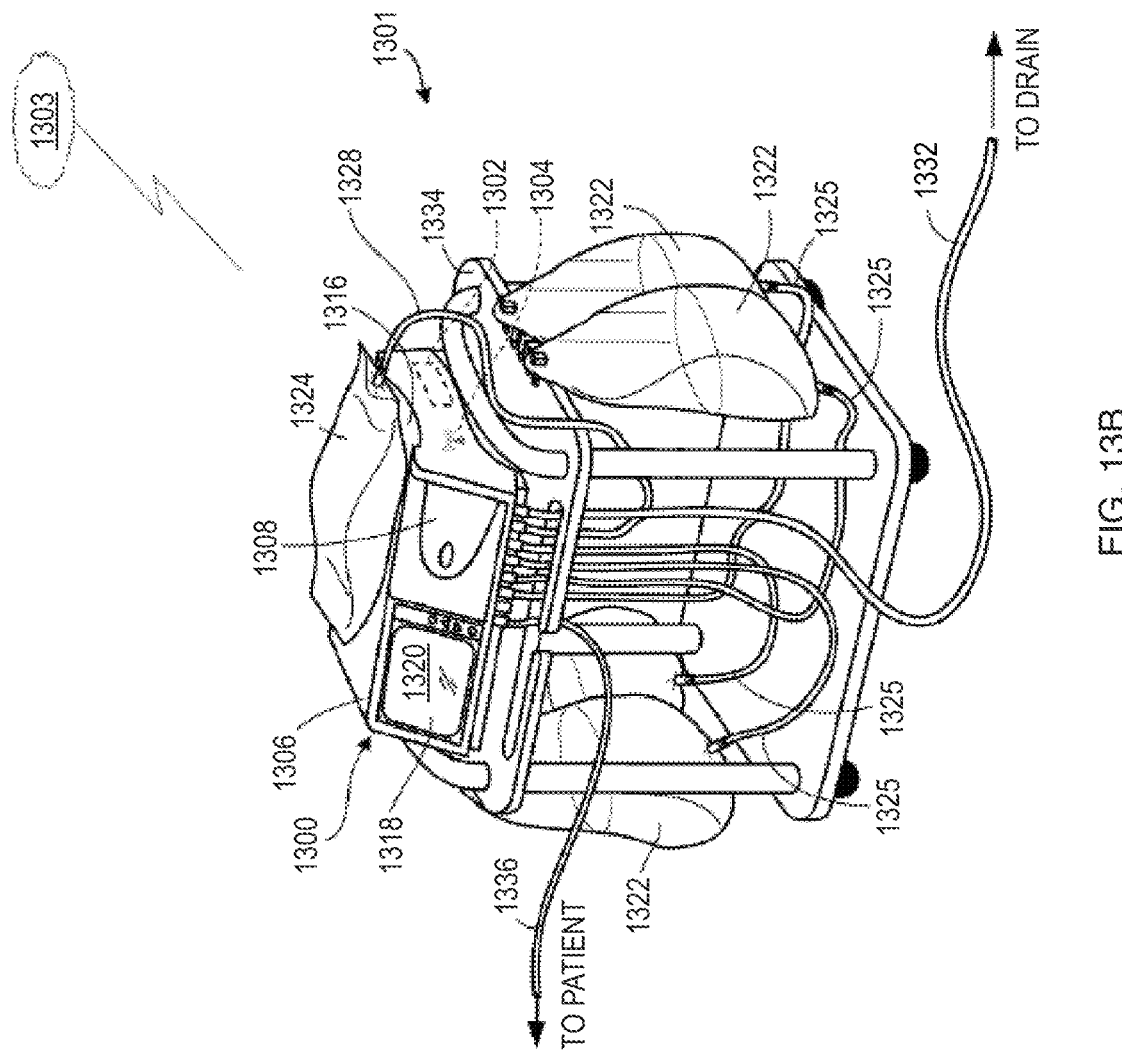
Figure 14:
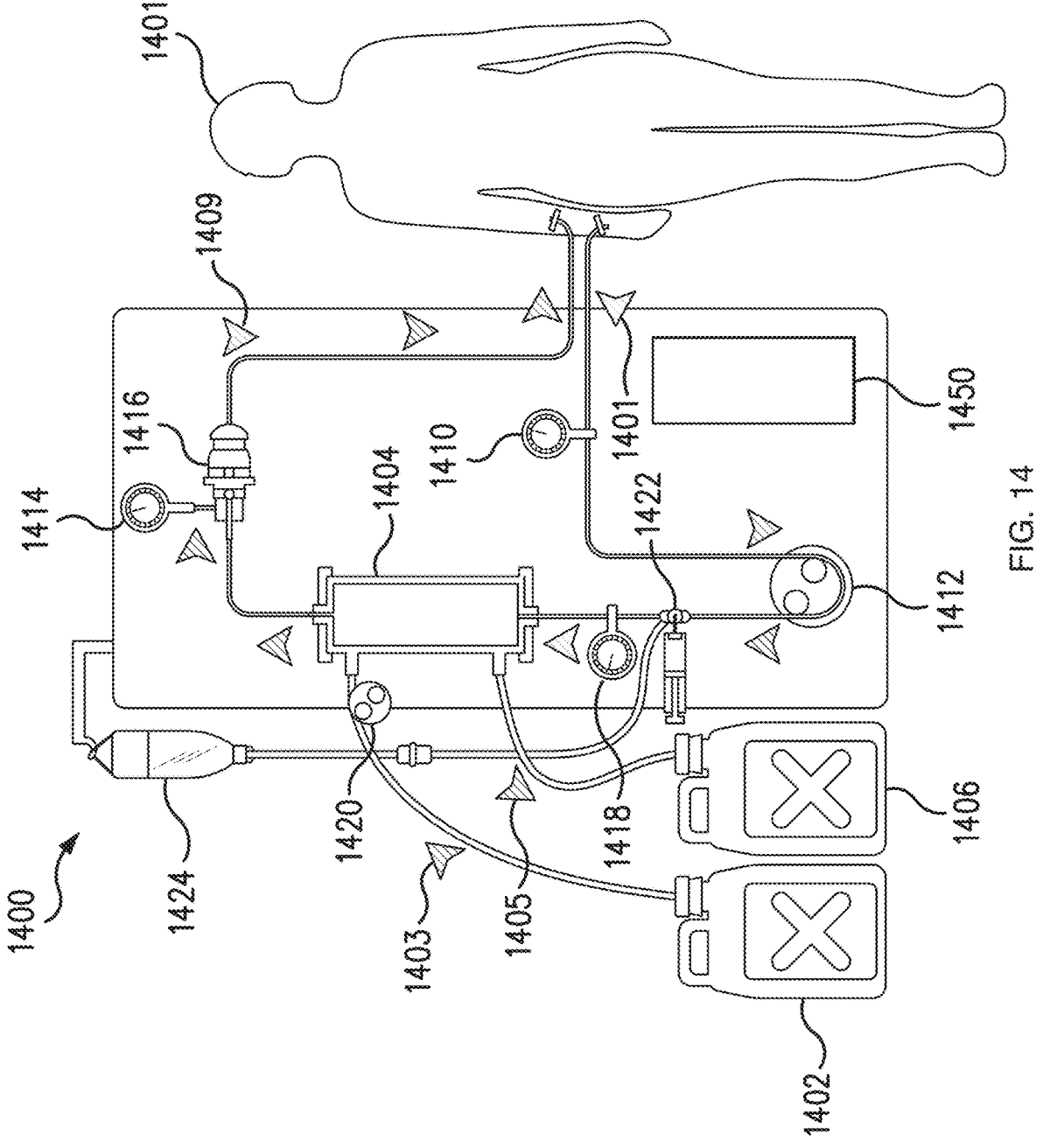
FIG. 14 is a diagram illustrating another exemplary embodiment of a dialysis system in accordance with the present disclosure.

FIGS. 13A-13B show an example of a peritoneal dialysis (PD) system 1301, which is configured in accordance with an exemplary embodiment of the system described herein. In some implementations, the PD system 1301 may be a home PD system, e.g., a PD system configured for use at a patient's home. The dialysis system 1301 may include a dialysis machine 1300 (e.g., a peritoneal dialysis machine 1300, also referred to as a PD cycler) and in some embodiments the machine may be seated on a cart 1304.

The dialysis machine 1302 may include a housing 1306, a door 1308, and a cartridge interface including pump heads 1342, 1344 for contacting a disposable cassette, or cartridge 1315, where the cartridge 1315 is located within a compartment formed between the cartridge interface and the closed door 1308 (e.g., cavity 1305). Fluid lines 1325 may be coupled to the cartridge 1315 in a known manner, such as via a connector, and may further include valves for controlling fluid flow to and from fluid bags including fresh dialysate and warming fluid. In another embodiment, at least a portion of the fluid lines 1325 may be integral to the cartridge 1315. Prior to operation, a user may open the door 1308 to insert a fresh cartridge 1315, and to remove the used cartridge 1315 after operation.

The cartridge 1315 may be placed in the cavity 1305 of the machine 1300 for operation. During operation, dialysate fluid may be flowed into a patient's abdomen via the cartridge 1315, and spent dialysate, waste, and/or excess fluid may be removed from the patient's abdomen via the cartridge 1315. The door 1308 may be securely closed to the machine 1300. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

A heater tray 1316 may be positioned on top of the housing 1306. The heater tray 1316 may be any size and shape to accommodate a bag of dialysate (e.g., a 5 L bag of dialysate) for batch heating. The dialysis machine 1300 may also include a user interface such as a touch screen 1318 and control panel 1320 operable by a user (e.g., a caregiver or a patient) to allow, for example, set up, initiation, and/or termination of a dialysis treatment. In some embodiments, the heater tray 1316 may include a heating element 1335, for heating the dialysate prior to delivery into the patient.

Dialysate bags 1322 may be suspended from hooks on the sides of the cart 1334, and a heater bag 1324 may be positioned in the heater tray 1316. Hanging the dialysate bags 1322 may improve air management as air content may be disposed by gravity to a top portion of the dialysate bag 1322. Although four dialysate bags 1322 are illustrated in FIG. 13B, any number "n" of dialysate bags may be connectable to the dialysis machine 1300 (e.g., 1 to 5 bags, or more), and reference made to first and second bags is not limiting to the total number of bags used in a dialysis system 1301. For example, the dialysis machine may have dialysate bags 1322a, . . . 1322n connectable in the system 1301. In some embodiments, connectors and tubing ports may connect the dialysate bags 1322 and lines for transferring dialysate. Dialysate from the dialysate bags 1322 may be transferred to the heater bag 1324 in batches. For example, a batch of dialysate may be transferred from the dialysate bags 1322 to the heater bag 1324, where the dialysate is heated by the heating element 1340. When the batch of dialysate has reached a predetermined temperature (e.g., approximately 98°-100° F., 37° C.), the batch of dialysate may be flowed into the patient. The dialysate bags 1322 and the heater bag 1324 may be connected to the cartridge 1315 via dialysate bag lines or tubing 1325 and a heater bag line or tubing 1328, respectively. The dialysate bag lines 1325 may be used to pass dialysate from dialysate bags 1322 to the cartridge during use, and the heater bag line 1328 may be used to pass dialysate back and forth between the cartridge and the heater bag 1324 during use. In addition, a patient line 1336 and a drain line 1332 may be connected to the cartridge 1315. The patient line 1336 may be connected to a patient's abdomen via a catheter and may be used to pass dialysate back and forth between the cartridge and the patient's peritoneal cavity by the pump heads 1342, 1344 during use. The drain line 1332 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 1325), or fluid lines, via a cartridge.

The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 1318 and the control panel 1320 may allow an operator to input various treatment parameters to the dialysis machine 1300 and to otherwise control the dialysis machine 1300. In addition, the touch screen 1318 may serve as a display. The touch screen 1318 may function to provide information to the patient and the operator of the dialysis system 1301. For example, the touch screen 1318 may display information related to a dialysis treatment to be applied to the patient, including information related to a prescription.

The dialysis machine 1300 may include a processing module 1302 that resides inside the dialysis machine 1300, the processing module 1302 being configured to communicate with the touch screen 1318 and the control panel 1320. The processing module 1302 may be configured to receive data from the touch screen 1318 the control panel 1320 and sensors, e.g., weight, air, flow, temperature, and/or pressure sensors, and control the dialysis machine 1300 based on the received data. For example, the processing module 1302 may adjust the operating parameters of the dialysis machine 1300.

The dialysis machine 1300 may be configured to connect to a network 1303. The connection to network 1303 may be via a wired and/or wireless connection. The dialysis machine 1300 may include a connection component 1304 configured to facilitate the connection to the network 1303. The connection component 1304 may be a transceiver for wireless connections and/or other signal processor for processing signals transmitted and received over a wired connection. Other medical devices (e.g., other dialysis machines) or components may be configured to connect to the network 1303 and communicate with the dialysis machine 1300.

The user interface portion such as the touch screen 1318 and/or display 1320 may include one or more buttons for selecting and/or entering user information. The touch screen 1318 and/or display 1320 may be operatively connected to a controller (not shown) and disposed in the machine 1300 for receiving and processing the inputs to operate the dialysis machine 1300.

In some embodiments, the machine 1200, 1300, 1400 may wirelessly transmit (e.g., via a wireless Internet connection), alternatively or simultaneously or in coordination with sending information to the integrated care system 220, 220', information or alerts to a remote location, including but not limited to a doctor's office, hospital, call center, and technical support. For example, the machine 1200, 1300, 1400 may provide real time remote monitoring of machine operation and patient parameters. The memory 1220 of the machine 1200, may store data, or the machine 1200, 1300, 1400 may transmit data to a local or remote server at scheduled intervals.

FIG. 14 illustrates a diagram of an exemplary embodiment of a dialysis system 1400 in accordance with the present disclosure. The dialysis system 1400 may be configured to provide hemodialysis treatment to a patient 1401. Fluid reservoir 1402 may deliver fresh dialysate to a dialyzer 1404 via tubing 1403, and reservoir 1406 may receive spent dialysate once it has passed through the dialyzer 1404 via tubing 1405. A hemodialysis operation may filter particulates and/or contaminates from a patient's blood through a patient external filtration device, for example, a dialyzer 1404. As the dialysate is passed through the dialyzer 1404, so too unfiltered patient blood is passed into the dialyzer via tubing 1407 and filtered blood is returned to the patient via tubing 1409. Arterial pressure may be monitored via pressure sensor 1410, inflow pressure monitored via sensor 1418, and venous pressure monitored via pressure sensor 1414. An air trap and detector 1416 may ensure that air is not introduced into patient blood as it is filtered and returned to the patient 1401. The flow of blood and the flow of dialysate are controlled via respective pumps, including a blood pump 1412 and a fluid pump 1420. Heparin 1422, a blood thinner, may be used in conjunction with saline 1424 to ensure blood clots do not form or occlude blood flow through the system.

In some embodiments, the dialysis system 1400 may include a controller 1450, which may be similar to the controller 1405 described above with respect to dialysis machines 1400, 1400. The controller 1450 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. The controller 1450 may also be operatively connected to and/or communicate with additional sensors or sensor systems, although the controller 1450 may use any of the data available on the patient's biologic functions or other patient parameters. For example, the controller 1450 may send patient data to the integrated care system 220, 220', for use in the one or more algorithms as data for extraction and processing for determining whether an ESRD patient is at risk for hospitalization.

Figure 15:
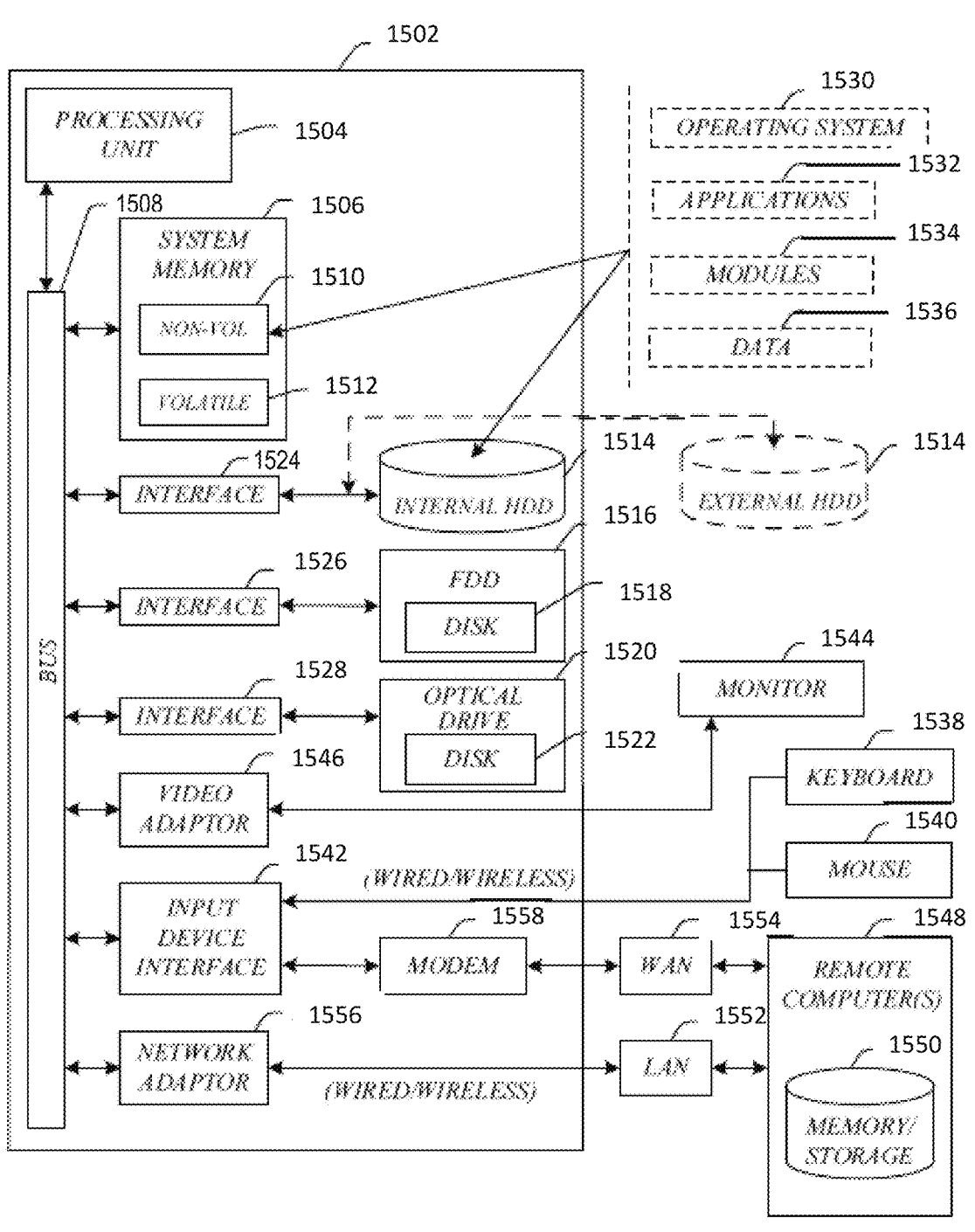
FIG. 15 is a block diagram illustrating an exemplary embodiment of a computing architecture in accordance with the present disclosure.

FIG. 15 illustrates an embodiment of an exemplary computing architecture 1500 suitable for implementing various embodiments as previously described. In various embodiments, the computing architecture 1500 may comprise or be implemented as part of an electronic device. In some embodiments, the computing architecture 1500 may be representative, for example, of computing device 410 and/or components of the platform 505 and/or integrated care system 220, 220'. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 15, the computing architecture 1500 comprises a processing unit 1504, a system memory 1506 and a system bus 1508. The processing unit 1504 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1504.

The system bus 1508 provides an interface for system components including, but not limited to, the system memory 1506 to the processing unit 1504. The system bus 1508 can be any of several types of bus structure that may further interconnect to a memory bus (with or without a memory controller), a peripheral bus, and a local bus using any of a variety of commercially available bus architectures. Interface adapters may connect to the system bus 1508 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1506 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 15, the system memory 1506 can include non-volatile memory 1510 and/or volatile memory 1512. A basic input/output system (BIOS) can be stored in the non-volatile memory 1510.

The computer 1502 may include various types of computer-readable storage media in the form of one or more lower speed memory units, including an internal (or external) hard disk drive (HDD) 1514, a magnetic floppy disk drive (FDD) 1516 to read from or write to a removable magnetic disk 1518, and an optical disk drive 1520 to read from or write to a removable optical disk 1522 (e.g., a CD-ROM or DVD). The HDD 1514, FDD 1516 and optical disk drive 1520 can be connected to the system bus 1508 by a HDD interface 1524, an FDD interface 1526 and an optical drive interface 1528, respectively. The HDD interface 1524 for external drive implementations can include at least one or both of Universal Serial Bus (USB) and IEEE 884 interface technologies.

The drives and associated computer-readable media provide volatile and/or nonvolatile storage of data, data structures, computer-executable instructions, and so forth. For example, a number of program modules can be stored in the drives and memory units 1510, 1512, including an operating system 1530, one or more application programs 1532, other program modules 1534, and program data 1536. In one embodiment, the one or more application programs 1532, other program modules 1534, and program data 1536 can include, for example, the various applications and/or components of system and/or apparatus 200, 200', 220, 220', 400, 500.

A user can enter commands and information into the computer 1502 through one or more wire/wireless input devices, for example, a keyboard 1528 and a pointing device, such as a mouse 1540. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1504 through an input device interface 1542 that is coupled to the system bus 1508, but can be connected by other interfaces such as a parallel port, IEEE 894 serial port, a game port, a USB port, an IR interface, and so forth.

A monitor 1544 or other type of display device is also connected to the system bus 1508 via an interface, such as a video adaptor 1546. The monitor 1544 may be internal or external to the computer 802. In addition to the monitor 1544, a computer typically includes other peripheral output devices, such as speakers, printers, and so forth.

The computer 1502 may operate in a networked environment using logical connections via wire and/or wireless communications to one or more remote computers, such as a remote computer 1548. The remote computer 1548 can be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1550 is illustrated. The logical connections depicted include wire/wireless connectivity to a local area network (LAN) 1552 and/or larger networks, for example, a wide area network (WAN) 1554. Such LAN and WAN networking environments are commonplace in offices and companies, and facilitate enterprise-wide computer networks, such as intranets, all of which may connect to a global communications network, for example, the Internet.

When used in a LAN networking environment, the computer 1502 is connected to the LAN 1552 through a wire and/or wireless communication network interface or adaptor 1556. The adaptor 1556 can facilitate wire and/or wireless communications to the LAN 1552, which may also include a wireless access point disposed thereon for communicating with the wireless functionality of the adaptor 1556.

When used in a WAN networking environment, the computer 1502 can include a modem 1558, or is connected to a communications server on the WAN 1554, or has other means for establishing communications over the WAN 1554, such as by way of the Internet. The modem 1558, which can be internal or external and a wire and/or wireless device, connects to the system bus 1508 via the input device interface 1542. In a networked environment, program modules depicted relative to the computer 1502, or portions thereof, can be stored in the remote memory/storage device 1550. It will be appreciated that the network connections shown are exemplary and other means of establishing a communications link between the computers can be used.

The computer 1502 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

The invention claimed is:

1. A method, comprising:

extracting, by at least one computing device, historical patient data from one or more databases, wherein the historical patient data corresponds to a pool of patients having end stage renal disease (ESRD);

using, by the at least one computing device, a predictive machine learning model with the extracted historical patient data corresponding to the pool of ESRD patients, for each ESRD patient in the pool of ESRD patients, to generate a risk score indicating an expected probability of hospitalization within a predetermined time period and to identify a plurality of factors that contributed to the risk score;

identifying, by the at least one computing device, a subset of the pool of ESRD patients having respective expected probabilities of hospitalization that are higher than other ESRD patients in the pool of ESRD patients;

determining, by the at least one computing device, based on the extracted historical patient data corresponding to the pool of ESRD patients, for each ESRD patient of the subset of ESRD patients, at least one prominent factor from the plurality of factors that contributed to the risk score, wherein the at least one prominent factor is configured to support a determination of patient interventions to impact the expected probability of hospitalization, and wherein the at least one prominent factor for each ESRD patient of the pool of ESRD patients is identified using Shapley additive explanations; and determining and executing, by the at least one computing device, at least one clinical intervention for at least one ESRD patient of the pool of ESRD patients, wherein the at least one clinical intervention is configured to target the at least one prominent factor to lower the expected probability of hospitalization for the at least one ESRD patient, and wherein the at least one clinical intervention comprises at least one of:

(a) administering one or more dialysis treatments in addition to a patient's existing dialysis schedule, (b) extending a patient's dialysis treatment time, (c) adjusting a patient's target weight for a dialysis treatment, (d) adjusting a dialysate sodium concentration for a patient's dialysis treatment, or (e) adjusting a patient's blood pressure medication.

2. The method of claim 1, wherein the predetermined time period is 7 days or less.

3. The method of claim 1, wherein the extracted historical patient data corresponding to the pool of ESRD patients comprises a patient demographics.

4. The method of claim 3, wherein the patient demographics comprise one or more of: date of birth, date of first dialysis, gender, race, ethnicity, or marital status.

5. The method of claim 1, wherein the extracted historical patient data corresponding to the pool of ESRD patients comprises laboratory values, and wherein laboratory values comprise one or more of: hemoglobin level or albumin level.

6. The method of claim 5, wherein the laboratory values include one or more of: an average over a specified time period, a maximum value, a minimum value, a value spike, a value dip, or trending values.

7. The method of claim 1, wherein the extracted historical patient data corresponding to the pool of ESRD patients comprises treatment data, wherein the treatment data comprises vitals, and wherein the vitals include one or more of: an average over a specified time period, a maximum value, a minimum value, a value spike, a value dip, or trending values.

8. The method of claim 1, wherein the extracted historical patient data corresponding to the pool of ESRD patients comprises a comprehensive assessment, wherein the comprehensive assessment comprises one or more of: recent hospitalization history, a history of a missed appointments, notes, complaints, medical professional assessments, or delivered medications.

9. The method of claim 1, further comprising:

generating a report that ranks the pool of ESRD patients according to their respective expected probabilities of hospitalization, wherein the report also provides the at least one prominent factor for each respective ESRD patient.

10. The method of claim 9, further comprising:

providing the generated report to one or more health care providers.

11. The method of claim 1, further comprising:

transmitting an automated alert to one or more health care providers, based on the expected probabilities of hospitalization.

12. The method of claim 1, wherein the pool of ESRD patients are patients of an ESRD Seamless Care Organization (ESCO).

13. A system, comprising:

one or more databases configured to store historical patient data, wherein the historical patient data corresponds to a pool of patients having end stage renal disease (ESRD); and at least one computing device configured to:

extract the historical patient data from the one or more databases;

use a predictive machine learning model with the extracted historical patient data corresponding to the pool of ESRD patients, for each ESRD patient in the pool of ESRD patients, to generate a risk score indicating an expected probability of hospitalization within a predetermined time period and to identify a plurality of factors that contributed to the risk score;

identify a subset of the pool of ESRD patients having respective expected probabilities of hospitalization that are higher than other ESRD patients in the pool of ESRD patients;

determine, based on the extracted historical patient data corresponding to the pool of ESRD patients, for each ESRD patient of the subset of ESRD patients, at least one prominent factor from the plurality of factors that contributed to the risk score, wherein the at least one prominent factor is configured to support a determination of patient interventions to impact the expected probability of hospitalization, and wherein the at least one prominent factor for each ESRD patient of the pool of ESRD patients is identified using Shapley additive explanations; and determine and execute at least one clinical intervention for at least one ESRD patient of the pool of ESRD patients, wherein the at least one clinical intervention is configured to target the at least one prominent factor to lower the expected probability of hospitalization for the at least one ESRD patient, and wherein the at least one clinical intervention comprises at least one of:

(a) administering one or more dialysis treatments in addition to a patient's existing dialysis schedule, (b) extending a patient's dialysis treatment time, (c) adjusting a patient's target weight for a dialysis treatment, (d) adjusting a dialysate sodium concentration for a patient's dialysis treatment, or (e) adjusting a patient's blood pressure medication.

14. The system of claim 13, wherein the predetermined time period is 7 days or less.

15. The system of claim 13, wherein the at least one computing device is further configured to:

generate a report that ranks the pool of ESRD patients according to their respective expected probabilities of hospitalization, wherein the report also provides the at least one prominent factor for each respective ESRD patient.

16. The system of claim 13, wherein the at least one computing device is further configured to:

transmit an automated alert to one or more health care providers, based on the expected probabilities of hospitalization.

17. One or more non-transitory computer-readable mediums having processor-executable instructions stored thereon, wherein the processor-executable instructions, when executed, facilitate performance of the following:

extracting, by at least one computing device, historical patient data from one or more databases, wherein the historical patient data corresponds to a pool of patients having end stage renal disease (ESRD);

using, by the at least one computing device, a predictive machine learning model with the extracted historical patient data corresponding to the pool of ESRD patients, for each ESRD patient in the pool of ESRD patients, to generate a risk score indicating an expected probability of hospitalization within a predetermined time period and to identify a plurality of factors that contributed to the risk score;

identifying, by the at least one computing device, a subset of the pool of ESRD patients having respective expected probabilities of hospitalization that are higher than other ESRD patients in the pool of ESRD patients;

determining, by the at least one computing device, based on the extracted historical patient data corresponding to the pool of ESRD patients, for each ESRD patient of the subset of ESRD patients, at least one prominent factor from the plurality of factors that contributed to the risk score, wherein the at least one prominent factor is configured to support a determination of patient interventions to impact the expected probability of hospitalization, and wherein the at least one prominent factor for each ESRD patient of the pool of ESRD patients is identified using Shapley additive explanations; and determining and executing, by the at least one computing device, at least one clinical intervention for at least one ESRD patient of the pool of ESRD patients, wherein the at least one clinical intervention is configured to target the at least one prominent factor to lower the expected probability of hospitalization for the at least one ESRD patient, and wherein the at least one clinical intervention comprises at least one of:

(a) administering one or more dialysis treatments in addition to a patient's existing dialysis schedule, (b) extending a patient's dialysis treatment time, (c) adjusting a patient's target weight for a dialysis treatment, (d) adjusting a dialysate sodium concentration for a patient's dialysis treatment, or (e) adjusting a patient's blood pressure medication.

18. The one or more non-transitory computer-readable mediums of claim 17, wherein the predetermined time period is 7 days or less.

19. The one or more non-transitory computer-readable mediums of claim 17, wherein the processor-executable instructions, when executed, further facilitate performance of the following:

generating a report that ranks the pool of ESRD patients according to their respective expected probabilities of hospitalization, wherein the report also provides the at least one prominent factor for each respective ESRD patient.

20. The one or more non-transitory computer-readable mediums of claim 17, wherein the processor-executable instructions, when executed, further facilitate performance of the following:

transmitting an automated alert to one or more health care providers, based on the expected probabilities of hospitalization.

* * * * *